(12) United States Patent
Samatar et al.

(10) Patent No.: US 9,229,008 B2
(45) Date of Patent: Jan. 5, 2016

(54) IL-8 LEVEL AS A DETERMINANT OF RESPONSIVITY OF A CANCER TO TREATMENT

(71) Applicant: Merck Sharp & Dohme Corp., Rahway, NJ (US)

(72) Inventors: Ahmed A. Samatar, West Windsor, NJ (US); Brian Long, Natick, MA (US); Priya Dayananth, Summit, NJ (US); Diane Levitan, Tenafly, NJ (US); Marsha Smith, Princeton, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 58 days.

(21) Appl. No.: 14/036,857

(22) Filed: Sep. 25, 2013

(65) Prior Publication Data

US 2014/0018367 A1 Jan. 16, 2014

Related U.S. Application Data

(62) Division of application No. 13/059,796, filed as application No. PCT/US2009/054021 on Aug. 17, 2009, now Pat. No. 8,586,543.

(60) Provisional application No. 61/090,073, filed on Aug. 19, 2008.

(51) Int. Cl.
  *G01N 33/53* (2006.01)
  *A61K 38/00* (2006.01)
  *A61K 45/00* (2006.01)
  *G01N 33/68* (2006.01)
  *G01N 33/574* (2006.01)

(52) U.S. Cl.
  CPC ...... *G01N 33/6869* (2013.01); *G01N 33/57407* (2013.01); *G01N 2333/5421* (2013.01); *G01N 2800/52* (2013.01)

(58) Field of Classification Search
  None
  See application file for complete search history.

(56) References Cited

U.S. PATENT DOCUMENTS

| | | |
|---|---|---|
| 2005/0048533 A1 | 3/2005 | Sidransky et al. |
| 2007/0191604 A1 | 8/2007 | Cooper et al. |
| 2007/0259375 A1 | 11/2007 | Ford et al. |
| 2008/0131885 A1 | 6/2008 | Pratilas et al. |
| 2009/0118284 A1 | 5/2009 | Cooper et al. |
| 2011/0158944 A1 | 6/2011 | Hosted et al. |

FOREIGN PATENT DOCUMENTS

| | | |
|---|---|---|
| WO | WO2005/102387 | 11/2005 |
| WO | WO2007/070398 | 6/2007 |
| WO | WO2007/097937 | 8/2007 |
| WO | WO2007/125330 | 11/2007 |
| WO | WO2008/133641 | 11/2008 |
| WO | WO2008/153858 | 12/2008 |
| WO | WO2009/073513 | 6/2009 |
| WO | WO2009/105500 | 8/2009 |

OTHER PUBLICATIONS

Ball DW, Jin N, Rosen DM, Dackiw A, Sidransky D, Xing M, Nelkin BD.Selective growth inhibition in BRAF mutant thyroid cancer by the mitogen-activated protein kinase kinase 1/2 inhibitor AZD6244. J Clin Endocrinol Metab. Dec. 2007;92(12):4712-18. Epub Sep. 18, 2007.

Liang et al., Targeting mutant (V600E) B-Raf in melanoma Interrupts immunoediting of leukocyte functions and melanoma extravasation. Ca.Res. 67, 5814-5820, 2007.

Wang et al., Induction of interleukin-8 secretion and activation of ERK1/2, p38 MAPK signaling pathways by thrombin in dermal fibroblasts. Int. J. Biochem. Cell Biol., 38, 1571-1583,2006.

Yarden et al. SnapShot: EGFR signaling pathway Cell, 131, 1018-1018e1, 2007.

Christensen JG, Vincent PW, Klohs WD, Fry DW, Leopold WR, Elliott WL. Plasma vascular endothelial growth factor and interleukin-8 as biomarkers of antitumor efficacy of a prototypical erbB family tyrosine kinase inhibitor. Mol Cancer Ther. Jun. 2005;4(6):938-47.

Krzystek-Korpacka M, Matusiewicz M, Diakowska D, Grabowski K, Blachut K, Konieczny D, Kustrzeba-Wojcicka I, Terlecki G, Banas T. Elevation of circulating interleukin-8 is related to lymph node and distant metastases in esophageal squamous cell carcinomas—implication for clinical evaluation of cancer patient. Ctyokine. Mar. 2008;41(3):232-9. Epub Jan. 7, 2008.

Varney et al. Serum levels of interleukin-8 directly correlates with tumor burden, angiogenesis and metastasis in human malignant melanoma cells xenografted in nude mice. Clinical & Experimental Metastasis 19(suppl1): 2 (2002).

Molica S, Vitelli G, Levato D, Levato L, Dattilo A, Gandolfo GM. Ciinico-biological implications of increased serum levels of interleukin-8 in B-cell chronic lymphocytic leukemia. Haematologica. Mar. 1999;84(3):208-11.

Kuku I, Bayraktar MR, Kaya E, Erkurt MA, Bayraktar N, Cikim K, Aydogdu I. Serum proinflammatory mediators at different periods of therapy in patients with multiple myeloma. Mediators Inflamm. Aug. 14, 2005;2005(3):171-4.

Subramaniam, D. A novel synthetic diphenyl, difluoroketone (L-2395) compound with potent in vitro and in vivo anti-cancer activity. Gastroenterology; v:130 i:4 p:A580; Apr. 2006.

Crawford S, Belajic D, Wei J, Riley JP, Dunford PJ, Bembenek S, Fourie A, Edwards, JP, Karlsson L, Brunmark A, Wolin RL, Blevitt JM.A novel B-RAF inhibitor blocks interleukin-8 (IL-8) synthesis in human melanoma xenografts, revealing IL-8 as a potential pharmacodynamic biomarker. Mol Cancer Ther. Mar. 2008;7(3):492-9.

Kumar A, Dubey D, Bansal P, Mandhani A, Naik S.Urinary interleukin-8 predicts the response of standard and low dose intravesical bacillus Calmette-Guerin (modified Danish 1331 strain) for superficial bladder cancer. J Urol. Nov. 2002;168(5):2232-5.

International Search Report, International Application No. PCT/US2009/54021 (2010).

*Primary Examiner* — Elly-Gerald Stoica

(57) ABSTRACT

The present application includes methods for using IL-8 as a biomarker for, e.g., tumor size, for example, during course of treatment with an anti-cancer agent such as an ERK inhibitor.

21 Claims, No Drawings

IL-8 LEVEL AS A DETERMINANT OF RESPONSIVITY OF A CANCER TO TREATMENT

This application is a divisional of U.S. patent application Ser. No. 13/059,796; filed Apr. 19, 2011, which claims the benefit of U.S. provisional patent application No. 61/090,073; filed Aug. 19, 2008, each of which is herein incorporated by reference in its entirety.

FIELD OF THE INVENTION

The present invention relates to methods of using IL-8 as a biomarker, inter alia, to monitor the effect of an ERK inhibitor on cancer.

BACKGROUND OF THE INVENTION

Mitogen activated protein (MAP) kinases include the extracellular signal regulated kinases 1 and 2 (ERK1 and ERK2). MAP kinases play a role in the regulation of biological processes including cell growth, proliferation, differentiation, inflammatory responses and programmed cell death. Unregulated activation of MAP kinases has been linked to cancer cell proliferation and tissue inflammation. Activation of ERK proteins often occurs through a process wherein a ligand-activated plasma membrane receptor facilitates the sequential activation of the Ras G-proteins, Raf kinases, and the MAP or ERK kinases-1 and 2 (MEK1/2), which are activators of ERK1 and ERK2.

Development of biomarkers for use in connection with anti-cancer chemotherapeutic agents has proven to be of enormous utility. For example, biomarkers may be employed to monitor, quickly and conveniently, the therapeutic effect of a given agent, for example, the effect of the inhibitor on the intracellular pathway it is targeting or the tumor it is treating. Biomarker genes that prove useful in the evaluation of a given agent often appear, at first glance, to be unrelated to the function of the molecular target of the agent. This makes the prediction of what biomarkers will be useful with a given agent difficult. For example, IL-8 is a pro-inflammatory cytokine whose upregualtion is associated with various inflammatory disorders. Any prediction that IL-8 may be useful for monitoring the efficacy of, for example, an ERK inhibitor, based on knowledge held in the art, would have been unlikely.

SUMMARY OF THE INVENTION

The present invention is based, in part, on the unlikely discovery that IL-8 is, in fact, useful for monitoring the effect of any anti-cancer agent, for example, an ERK inhibitor. Specifically, the present invention provides a method for monitoring tumor volume or status of a blood cancer, in a subject, comprising determining IL-8 levels, in the subject, over time; wherein tumor volume is determined to have increased or the blood cancer is determined to have progressed if IL-8 levels increased and wherein tumor volume is determined to have decreased or the blood cancer is determined to have regressed if IL-8 levels decreased. The present invention provides a method comprises monitoring the effect of an anti-cancer agent on tumor volume or blood cancer status in the body of a subject comprising administering said anti-cancer agent to the subject and monitoring said tumor volume or blood cancer status by the method set forth above; wherein the anti-cancer agent is determined to be effective if the agent is determined to have decreased tumor volume or to have regressed the blood cancer; and wherein the anti-cancer agent is determined not to be effective if the agent is determined not to have decreased tumor volume or not to have regressed the blood cancer. In an embodiment of the invention, the method comprises (i) measuring an IL-8 level in the body of said subject; (ii) administering one or more doses of said anti-cancer agent to said subject; (iii) measuring an IL-8 level in the body of said subject following said administration; and (iv) comparing the level of IL-8 measured in step (i) with the level of IL-8 measured in step (iii); wherein the anti-cancer agent is determined to be effective if the agent is determined to have decreased tumor volume or to have regressed the blood cancer; and wherein the anti-cancer agent is determined not to be effective if the agent is determined not to have decreased tumor volume or not to have regressed the blood cancer.

The present invention also provides a method for determining if a subject has a medical condition that is responsive to an anti-cancer agent comprising monitoring the effect of the anti-cancer agent by the method set forth above; wherein said condition is determined to be unresponsive to the anti-cancer agent if said agent is not determined to have decreased tumor volume or not to have regressed the blood cancer; or wherein the condition is determined to be responsive to the agent if said agent is determined to have decreased tumor volume or to have regressed the blood cancer. For example, in an embodiment of the invention, the method comprises: (i) measuring an IL-8 level in the body of said subject; (ii) administering one or more doses of said anti-cancer agent to said subject; (iii) measuring an IL-8 level in the body of said subject following said administration; (iv) comparing the level of IL-8 measured in step (i) with the level of IL-8 measured in step (iii); wherein said condition is determined to be unresponsive to the anti-cancer agent if said agent is not determined to have decreased tumor volume or not to have regressed the blood cancer; or wherein the condition is determined to be responsive to the agent if said agent is determined to have decreased tumor volume or to have regressed the blood cancer.

Furthermore, the present invention provides a method for evaluating dosage of an anti-cancer agent, in a subject with a tumor or blood cancer, comprising monitoring the effect of the anti-cancer agent, in the subject, by the method set forth above; wherein the dosage is determined to be sufficient if the agent decreases tumor volume or regresses the blood cancer; and wherein the dosage is determined to be insufficient if the agent does not decrease tumor volume or does not regress the blood cancer.

The present invention further provides a method for treating a tumor or blood cancer, in a subject, comprising administering a dose of an anti-cancer agent, to the subject, and monitoring the effect of the anti-cancer agent by the method set forth above; and, continuing treatment if the agent decreases tumor volume or regresses the blood cancer; or discontinuing treatment or increasing dosage administered if the agent does not decrease tumor volume or does not regress the blood cancer.

The present invention additionally provides a method for determining if an ERK inhibitor reduces ERK pathway activity comprising determining an IL-8 level, in a subject, following administration of the ERK inhibitor, to the subject; wherein the pathway is determined to be inhibited if the IL-8 level drops following administration of the ERK inhibitor and wherein the pathway is not determined to be inhibited if the IL-8 level is not observed to drop following administration of the ERK inhibitor.

In an embodiment of the invention, the anti-cancer agent is an ERK inhibitor, e.g., represented by a structural formula selected from the group consisting of:
(A1)
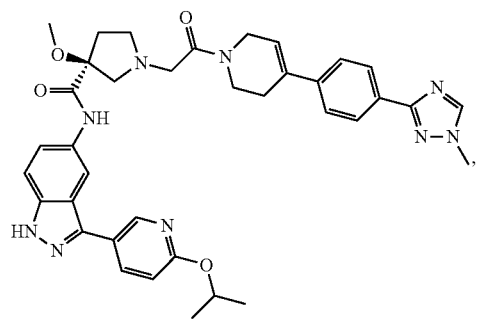
(A2)
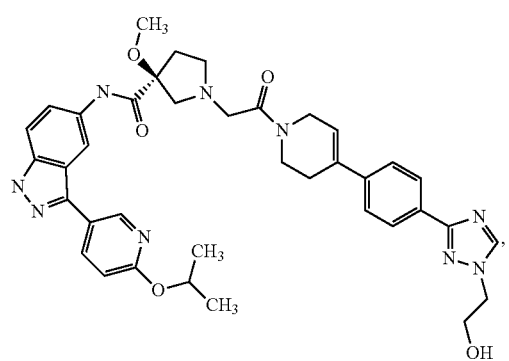
(A3)
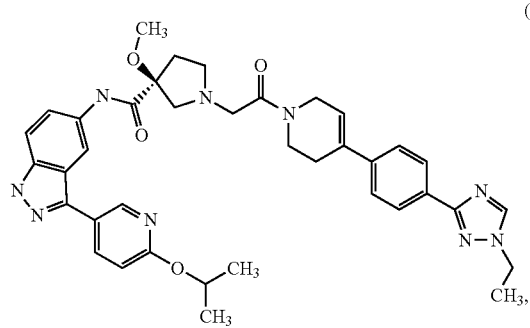
(A4)
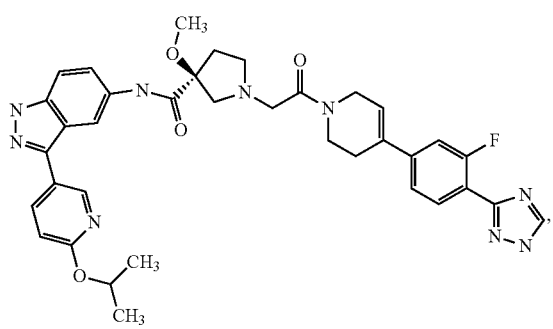
-continued
(A5)
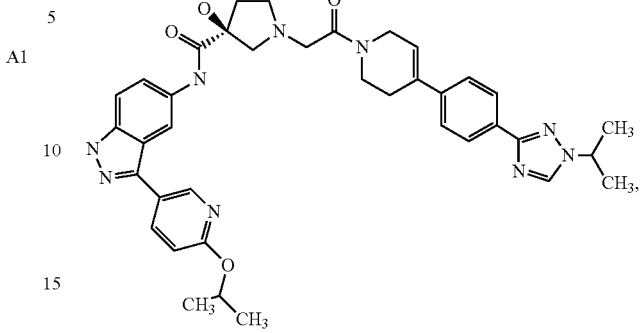
(A6)
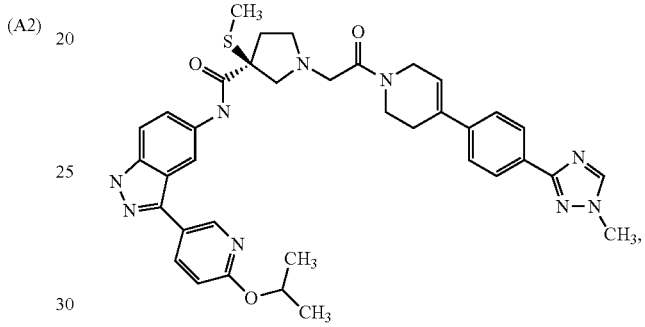
(A7)
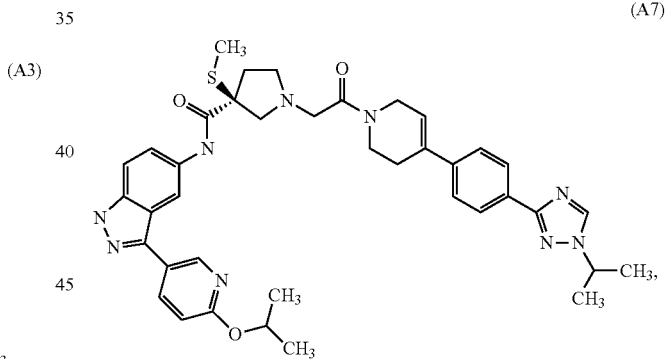
(A8)
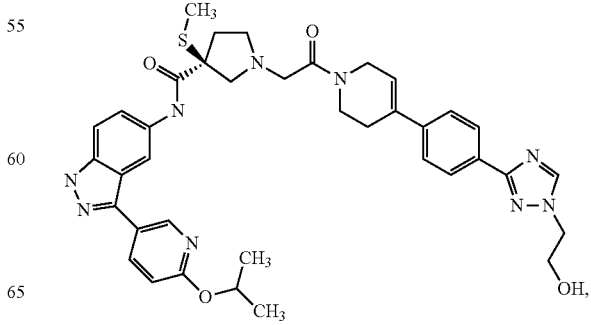

(A9)
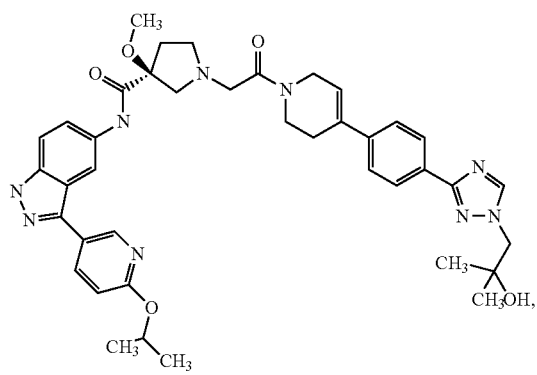
(A10)
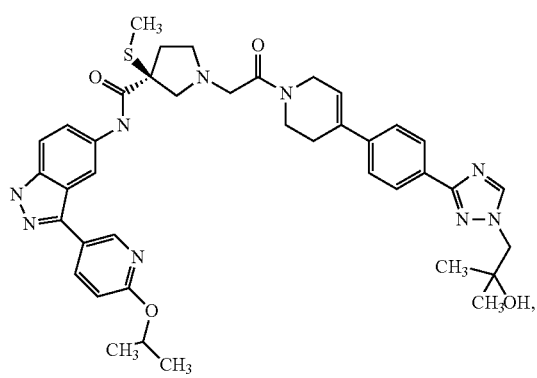
(A11)
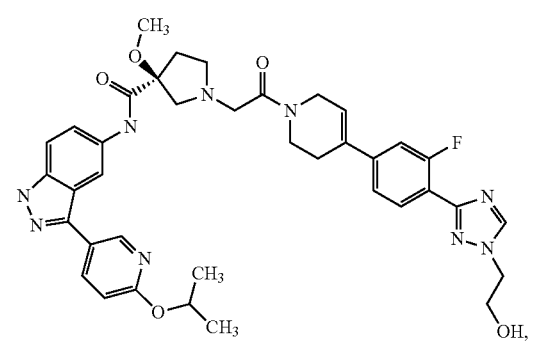
(A16)
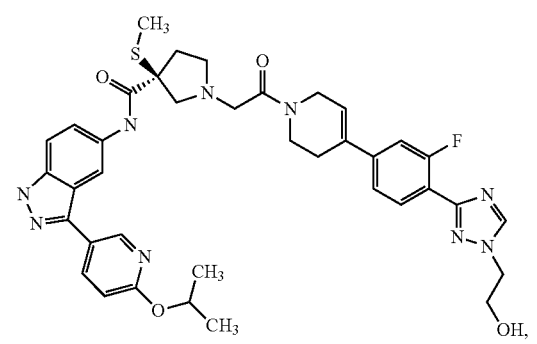
(A18)
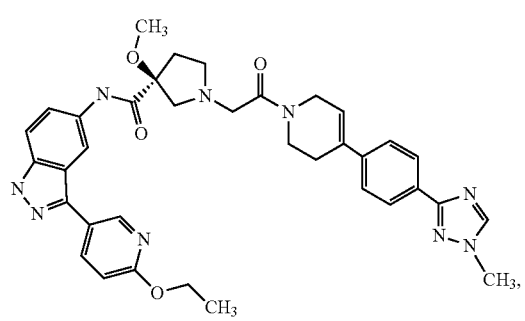
(A19)
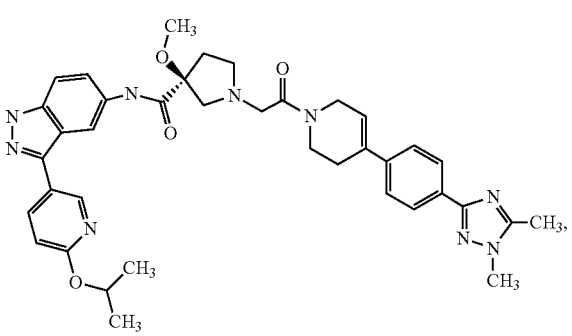
(A20)
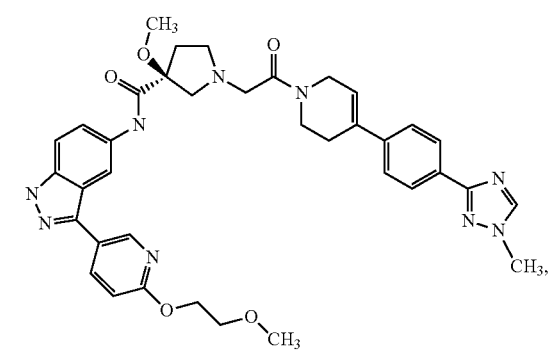
(A12)
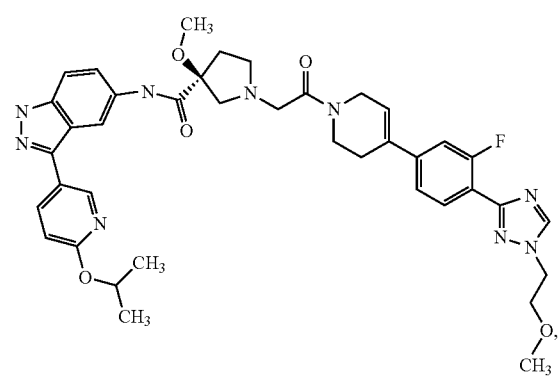

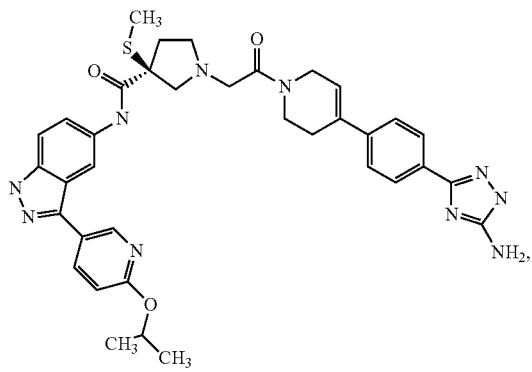
(A13)
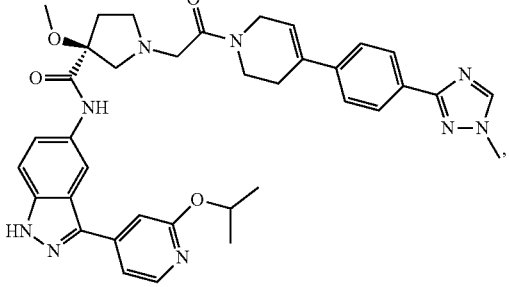
(A23)
(A14)
(A24)
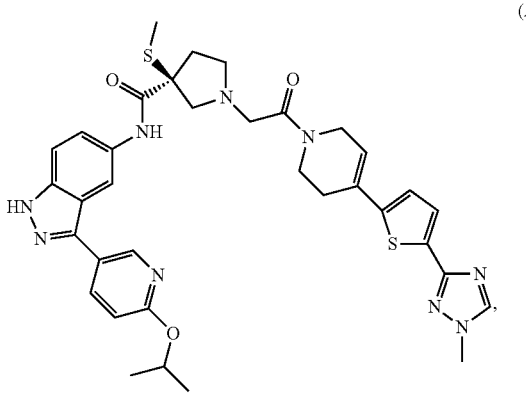
(A15)
(A25)
(A21)
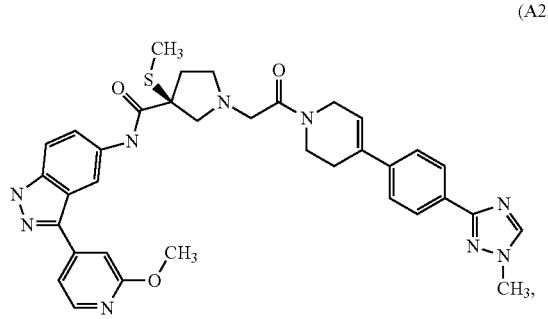
(A26)
(A22)
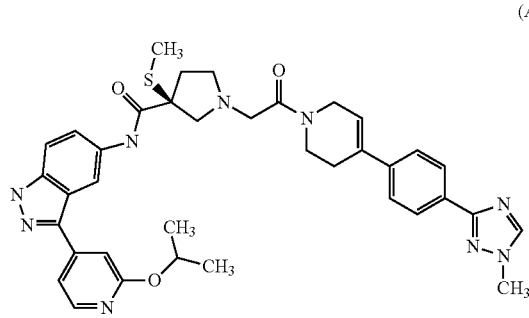
(A27)
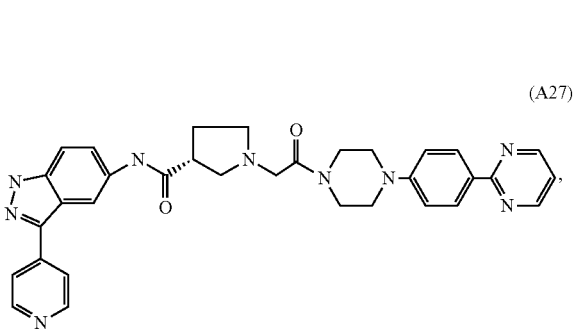

(A28)
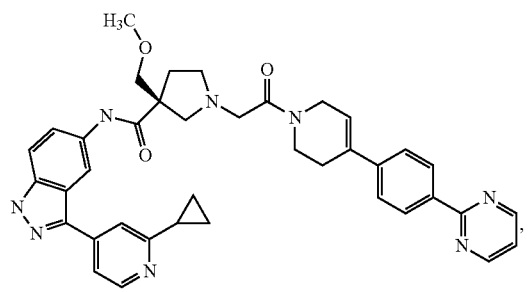
(A29)
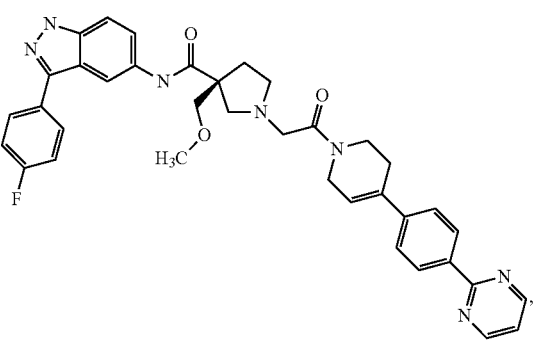
(A30)
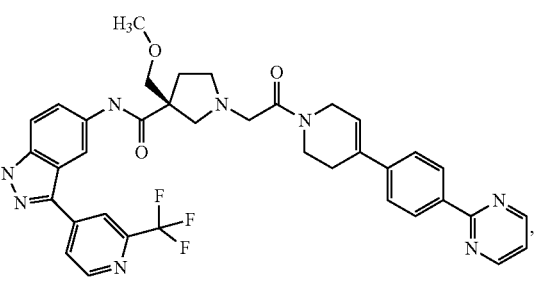
(A31)
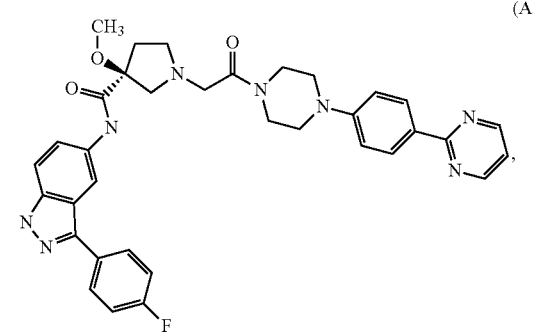
(A32)
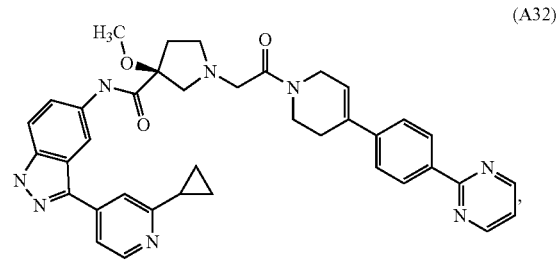
(A33)
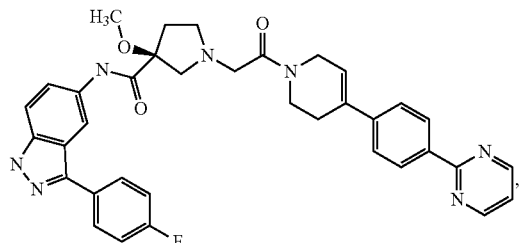
(A34)
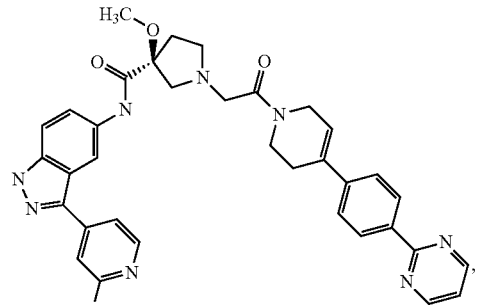
(A35)
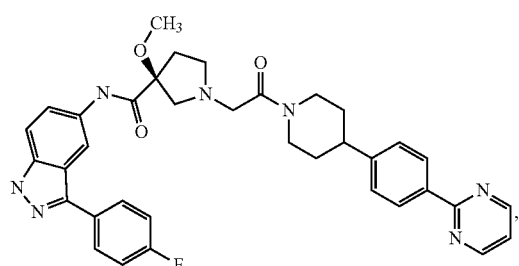
(A36)
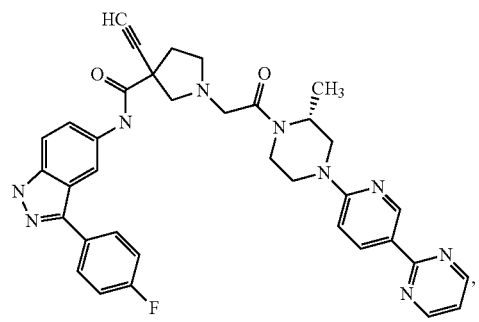
(A37)
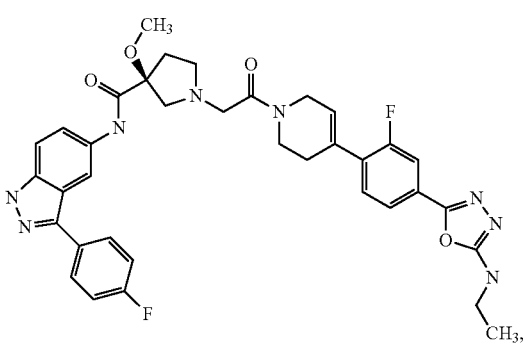

(A38)
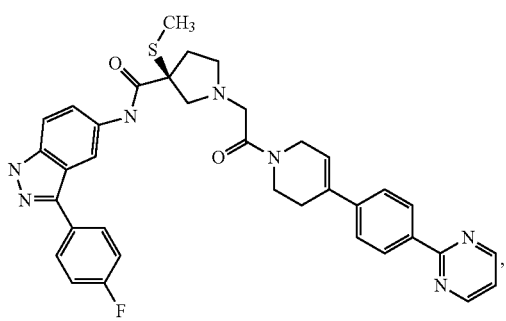

(A39)
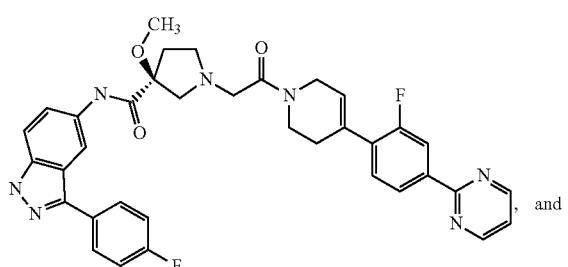
and (A40)
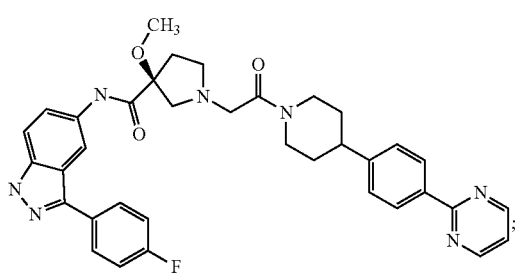

or any other ERK inhibitor, e.g., as discussed herein, e.g., under the section entitled "ERK inhibitors". In an embodiment of the invention, the medical condition or tumor or blood cancer is a member selected from the group consisting of: lung cancer, lung adenocarcinoma, non small cell lung cancer, pancreatic cancer, pancreatic carcinoma, exocrine pancreatic carcinoma, colon cancer, colorectal carcinoma, colon adenocarcinoma, colon adenoma, myeloid leukemia, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancer, squamous cell cancer of the head and neck, ovarian cancer, brain cancer, glioma, glioma blastoma multiforme, cancer of mesenchymal origin, fibrosarcoma, rhabdomyosarcoma, sarcoma, tetracarcinomas, neuroblastoma, kidney carcinoma, hepatoma, non-Hodgkin's lymphoma, multiple myeloma, and anaplastic thyroid carcinoma. In an embodiment of the invention, the medical condition or tumor or blood cancer is any such condition or tumor or cancer mediated by the expression and/or activity of ERK1 and/or ERK2.

DETAILED DESCRIPTION OF THE INVENTION

The present invention provides, for example, the use of IL-8 as a convenient, accurate biomarker for the effect an anti-cancer agent, such as an ERK inhibitor, is having on tumor volume or on the status of a blood cancer or on the activation level of the ERK signal transduction pathway. For example, rising IL-8 levels in the subject indicate rising tumor volume or blood cancer progression or rising ERK pathway induction; and decreasing IL-8 levels in the subject indicate decreasing tumor volume or blood cancer regression or decreasing ERK pathway induction. Steady IL-8 levels indicate steady tumor volume or blood cancer status or steady pathway induction levels. The fact that IL-8 is a secreted protein makes determination of IL-8 levels in the body of a subject simple since the levels can be determined in the subject's blood or plasma or other bodily fluids. The need for unduly invasive procedures for obtaining biomarker levels (e.g., biopsy) is eliminated through use of IL-8.

Blood cancer status refers to the clinical state of the blood cancer, e.g., progression, regression or maintenance of the blood cancer and/or the blood cancer signs, symptoms or clinical indicia.

The present invention also provides use of IL-8 as a marker which may be used to predict the sensitivity of a cell to an ERK inhibitor.

For example, an "anti-cancer agent" is any agent which provides any measurable alleviation of the signs, symptoms and/or clinical indicia of cancer (e.g., tumor growth or blood cancer progression) and/or the prevention, slowing or halting of progression or metastasis of cancer (e.g., melanoma) to any detectable degree. The term "subject" refers to a mammal, for example, a human or a mouse, rat, rabbit, dog, monkey, primate, hamster, horse or cat.

IL-8

The term IL-8 includes any human IL-8 gene or protein whatsoever. IL-8 is known by several names including, for example, interleukin-8, CXCL8, monocyte-derived neutrophil chemotactic factor, MDNCF, T-cell chemotactic factor, neutrophil-activating protein 1, NAP-1, Protein 3-10C, granulocyte chemotactic protein 1, GCP-1 or monocyte-derived neutrophil.

In an embodiment of the invention, IL-8 comprises the following amino acid sequence:

(SEQ ID NO: 2)
MTSKLAVALLAAFLISAALCEGAVLPRSAKELRCQCIKTYSKPFHPKFIK

ELRVIESGPHCANTEIIVKLSDGRELCLDPKENWVQRVVEKFLKRAENS

In an embodiment of the invention, IL-8 comprises the following nucleotide sequence:

(SEQ ID NO: 1)
atgacttcca agctggccgt ggctctcttg gcagccttcc tgatttctgc agctctgtgt gaaggtgcag ttttgccaag gagtgctaaa gaacttagat gtcagtgcat aaagacatac tccaaacctt tccaccccaa atttatcaaa gaactgagag tgattgagag tggaccacac tgcgccaaca cagaaattat tgtaaagctt tctgatggaa gagagctctg tctggacccc aaggaaaact gggtgcagag ggttgtggag aagtttttga agagggctga gaattcataa

ERK

The term "ERK" refers to any human ERK1 or ERK2 gene or protein whatsoever. ERK1 is known by several names including, for example, mitogen-activated protein kinase 3, extracellular signal-regulated kinase 1, insulin-stimulated MAP2 kinase, MAP kinase 1, MAPK 1, p44-ERK1, ERT2, p44-MAPK or microtubule-associated protein 2 kinase.

ERK2 is known by several names including, for example, mitogen-activated protein kinase 1, extracellular signal-regulated kinase 2, mitogen-activated protein kinase 2, MAP kinase 2, MAPK 2, p42-MAPK, or ERT1.

In an embodiment of the invention, ERK1 comprises the following amino acid sequence:

```
                                             (SEQ ID NO: 4)
MAAAAAQGGG GGEPRRTEGV GPGVPGEVEM VKGQPFDVGP

RYTQLQYIGE GAYGMVSSAY DHVRKTRVAI KKISPFEHQT

YCQRTLREIQ ILLRFRHENV IGIRDILRAS TLEAMRDVYI

VQDLMETDLY KLLKSQQLSN DHICYFLYQI LRGLKYIHSA

NVLHRDLKPS NLLINTTCDL KICDFGLARI ADPEHDHTGF

LTEYVATRWY RAPEIMLNSK GYTKSIDIWS VGCILAEMLS

NRPIFPGKHY LDQLNHILGI LGSPSQEDLN CIINMKARNY

LQSLPSKTKV AWAKLFPKSD SKALDLLDRM LTFNPNKRIT

VEEALAHPYL EQYYDPTDEP VAEEPFTFAM ELDDLPKERL

KELIFQETAR FQPGVLEAP
```

In an embodiment of the invention, ERK1 comprises the following nucleotide sequence:

```
                                             (SEQ ID NO: 3)
atggcggcgg cggcggctca gggggggcggg ggcggggagc cccgtagaac cgagggggtc ggcccggggg tcccggggga ggtggagatg gtgaaggggc agccgttcga cgtgggcccg cgctacacgc agttgcagta catcggcgag ggcgcgtacg gcatggtcag ctcggcctat gaccacgtgc gcaagactcg cgtggccatc aagaagatca gccccttcga acatcagacc tactgccagc gcacgctccg ggagatccaa atcctgctgc gcttccgcca tgagaatgtc atcggcatcc gagacattct gcgggcgtcc accctggaag ccatgagaga tgtctacatt gtgcaggacc tgatggagac tgacctgtac aagttgctga aaagccagca gctgagcaat gaccatatct gctacttcct ctaccagatc ctgcggggcc tcaagtacat ccactccgcc aacgtgctcc accgagatct aaagccctcc aacctgctca tcaacaccac ctgcgacctt aagatttgtg atttcggcct ggcccggatt gccgatcctg agcatgacca caccggcttc ctgacggagt atgtggctac gcgctggtac cgggccccag agatcatgct gaactccaag ggctatacca agtccatcga catctggtct gtgggctgca ttctggctga gatgctctct aaccggccca tcttccctgg caagcactac ctggatcagc tcaaccacat tctgggcatc ctgggctccc catcccagga
```
ggacctgaat tgtatcatca acatgaaggc ccgaaactac ctacagtctc tgccctccaa gaccaaggtg gcttgggcca agcttttccc caagtcagac tccaaagccc ttgacctgct ggaccggatg ttaaccttta accccaataa acggatcaca gtggaggaag cgctggctca cccctacctg gagcagtact atgacccgac ggatgagcca gtggccgagg agcccttcac cttcgccatg gagctggatg acctacctaa ggagcggctg aaggagctca tcttccagga gacagcacgc ttccagcccg gagtgctgga ggcccctag In an embodiment of the invention, ERK2 comprises the following amino acid sequence:

```
                                             (SEQ ID NO: 6)
MAAAAAAGAG PEMVRGQVFD VGPRYTNLSY IGEGAYGMVC

SAYDNVNKVR VAIKKISPFE HQTYCQRTLR EIKILLRFRH

ENIIGINDII RAPTIEQMKD VYIVQDLMET DLYKLLKTQH

LSNDHICYFL YQILRGLKYI HSANVLHRDL KPSNLLLNTT

CDLKICDFGL ARVADPDHDH TGFLTEYVAT RWYRAPEIML

NSKGYTKSID IWSVGCILAE MLSNRPIFPG KHYLDQLNHI

LGILGSPSQE DLNCIINLKA RNYLLSLPHK NKVPWNRLFP

NADSKALDLL DKMLTFNPHK RIEVEQALAH PYLEQYYDPS

DEPIAEAPFK FDMELDDLPK EKLKELIFEE TARFQPGYRS
```

In an embodiment of the invention, ERK2 comprises the following nucleotide sequence:

```
                                             (SEQ ID NO: 5)
atggcggcgg cggcggcggc gggcgcgggc ccggagatgg tccgcgggca ggtgttcgac gtggggccgc gctacaccaa cctctcgtac atcggcgagg gcgcctacgg catggtgtgc tctgcttatg ataatgtcaa caaagttcga gtagctatca agaaaatcag ccccttttgag caccagacct actgccagag aaccctgagg gagataaaaa tcttactgcg cttcagacat gagaacatca ttggaatcaa tgacattatt cgagcaccaa ccatcgagca aatgaaagat gtatatatag tacaggacct catggaaaca gatctttaca agctcttgaa gacacaacac ctcagcaatg accatatctg ctattttctc taccagatcc tcagagggtt aaaatatatc cattcagcta acgttctgca ccgtgacctc aagccttcca acctgctgct caacaccacc tgtgatctca agatctgtga ctttggcctg gcccgtgttg cagatccaga ccatgatcac acagggttcc tgacagaata tgtggccaca cgttggtaca gggctccaga aattatgttg aattccaagg gctacaccaa gtccattgat atttggtctg taggctgcat tctggcagaa atgctttcta acaggcccat
```

-continued

```
ctttccaggg aagcattatc ttgaccagct gaaccacatt
ttgggtattc ttggatcccc atcacaagaa gacctgaatt
gtataataaa tttaaaagct aggaactatt tgctttctct
tccacacaaa aataaggtgc catggaacag gctgttccca
aatgctgact ccaaagctct ggacttattg gacaaaatgt
tgacattcaa cccacacaag aggattgaag tagaacaggc
tctggcccac ccatatctgg agcagtatta cgacccgagt
gacgagccca tcgccgaagc accattcaag ttcgacatgg
aattggatga cttgcctaag gaaaagctca aagaactaat
tttttgaagag actgctagat tccagccagg atacagatct
taa
```

ERK Inhibitors

The present invention relates to methods for using ERK inhibitors to inhibit ERK1 and/or ERK2. An ERK inhibitor is any compound which inhibits any ERK1 and/or ERK2 activity (e.g., phosphorylation of p90 Ribosomal S6 Kinase (RSK), phosphorylation of c-jun, phosphorylation of c-myc or phosphorylation of Ets) or which is an anti-cancer agent which operates via inhibition of the ERK signal transduction pathway. In an embodiment of the invention, such ERK inhibitors are represented by a structural formula selected from the group consisting of:

(A1)

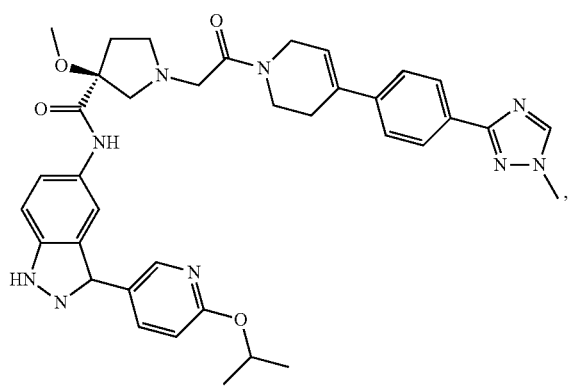

(A2)

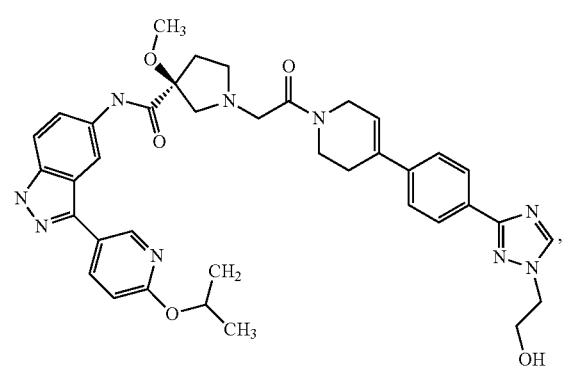

(A3)

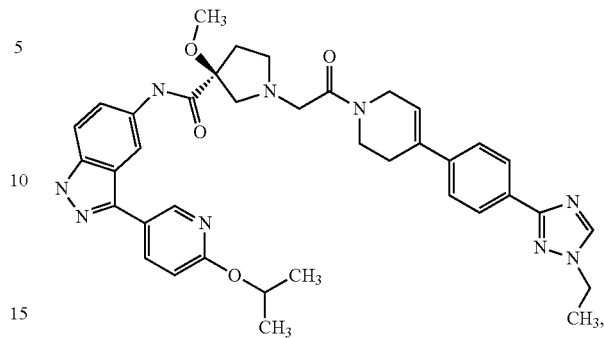

(A4)

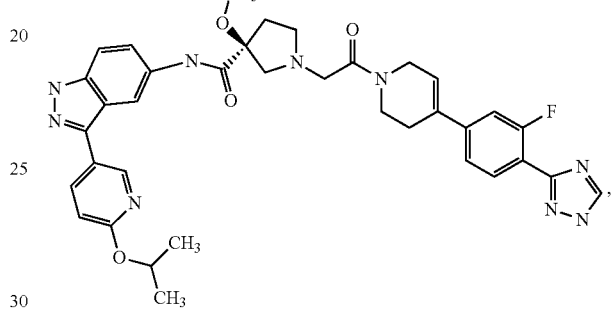

(A5)

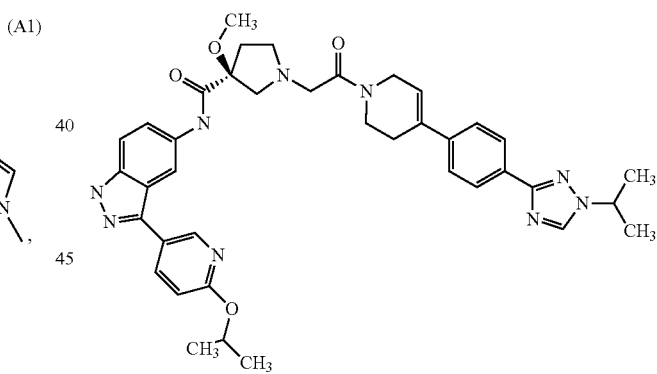

(A6)

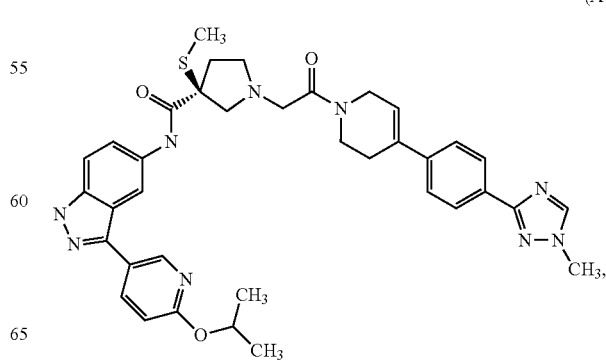

(A7)
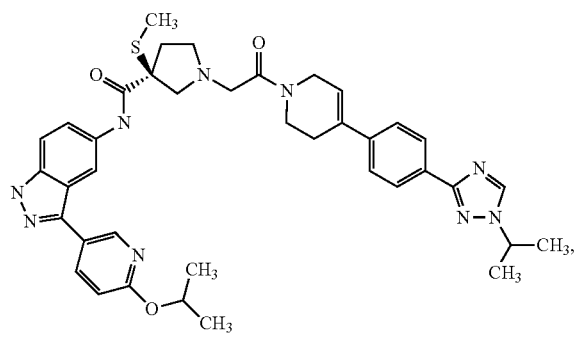
(A8)
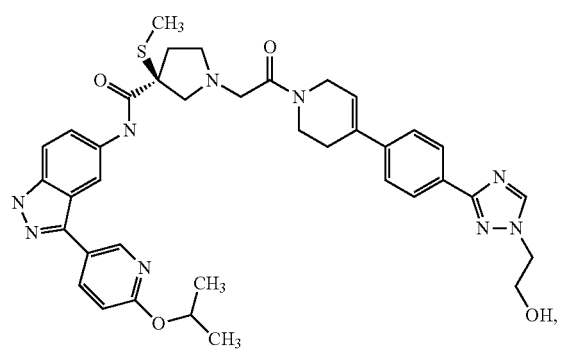
(A9)
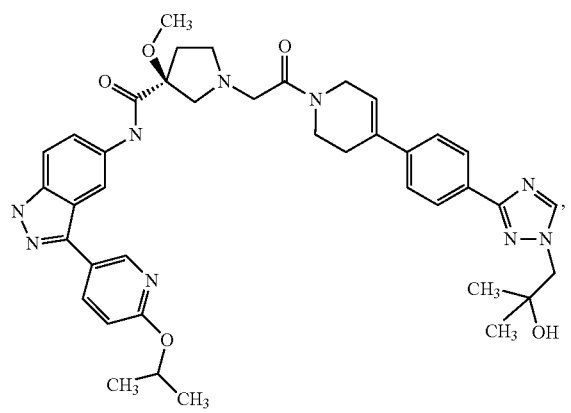
(A10)
(A11)
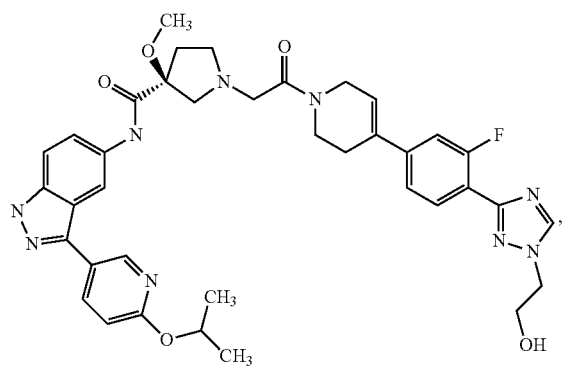
(A12)
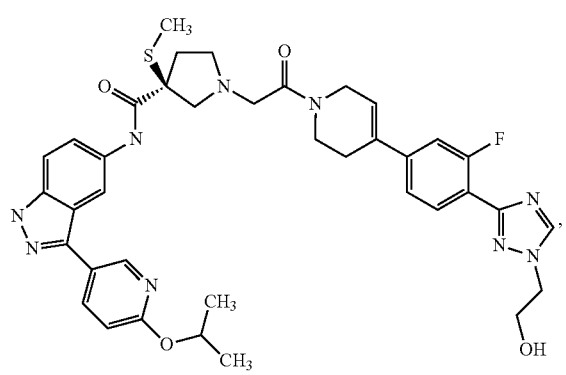
(A13)
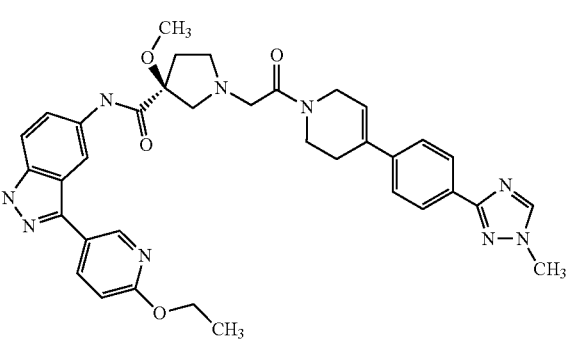
(A14)
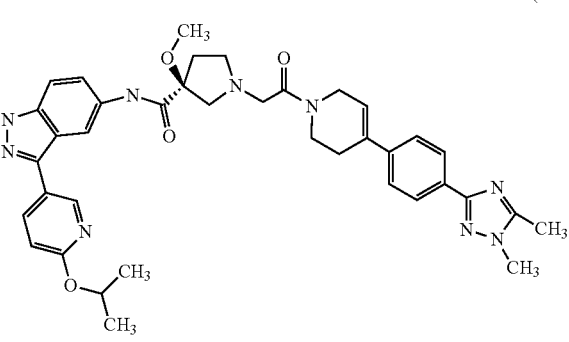

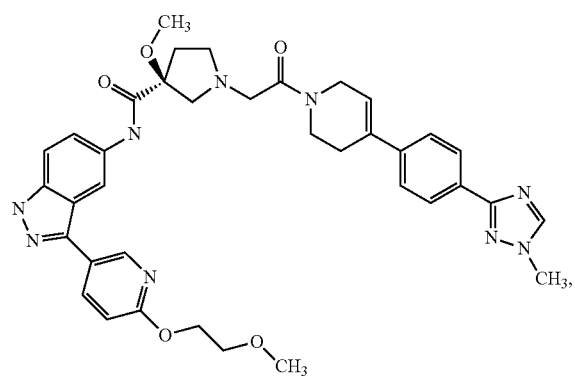
(A15)
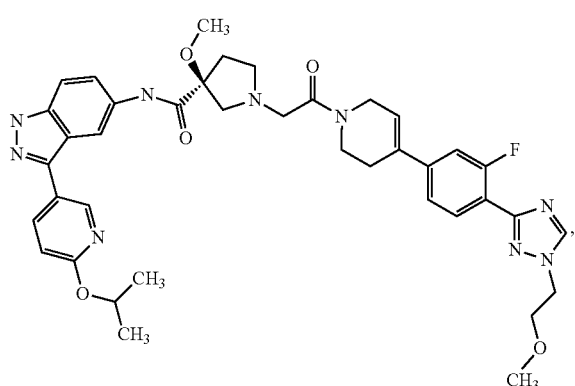
(A16)
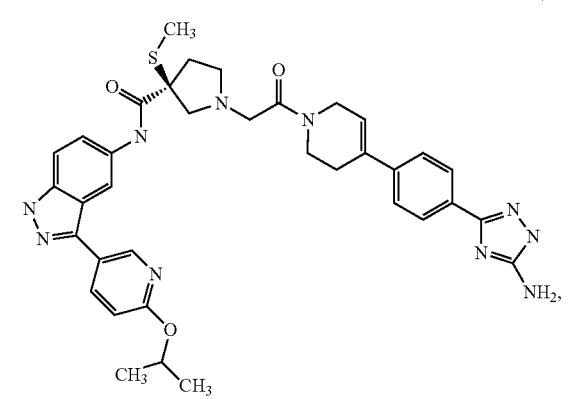
(A18)
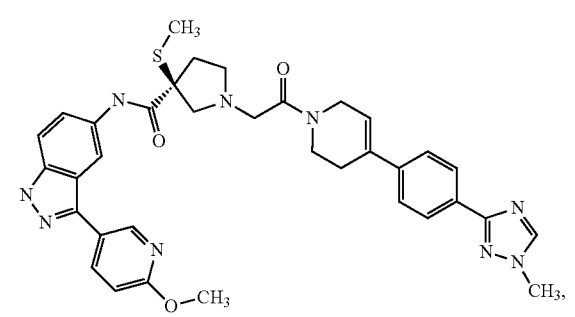
(A19)
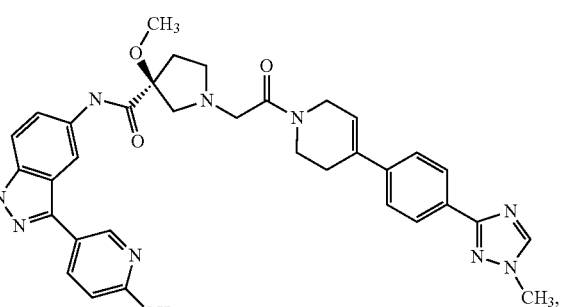
(A20)
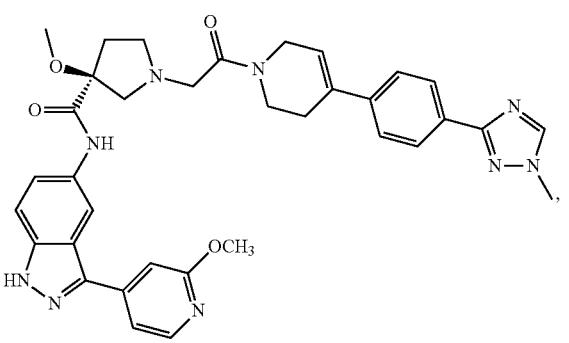
(A21)
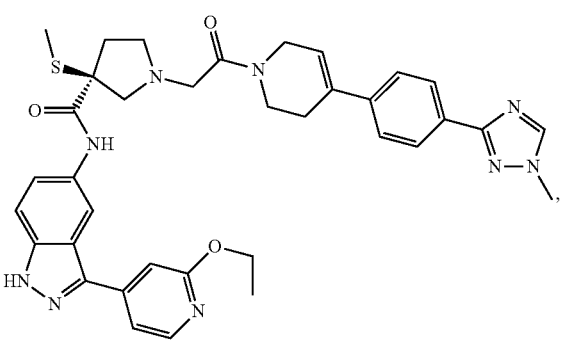
(A22)
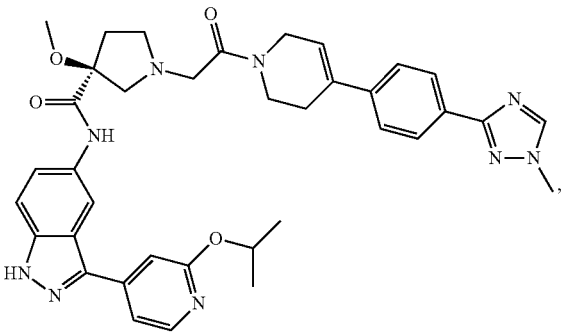
(A23)

(A24)
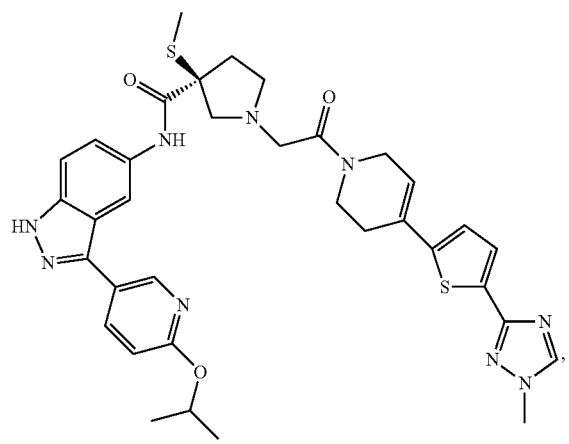
(A25)
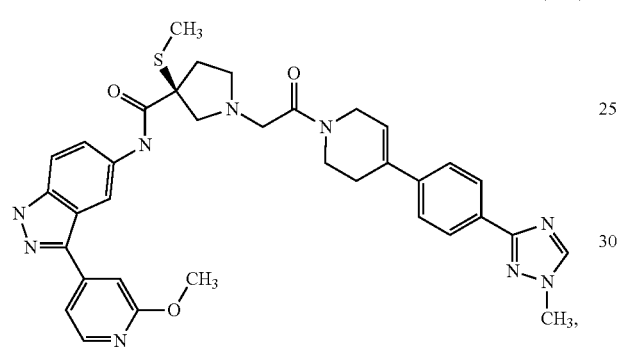
(A26)
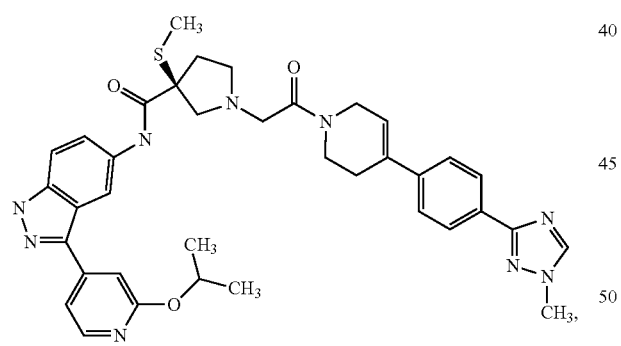
(A27)
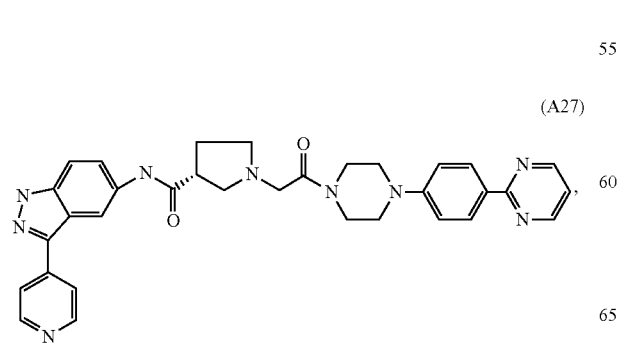
(A28)
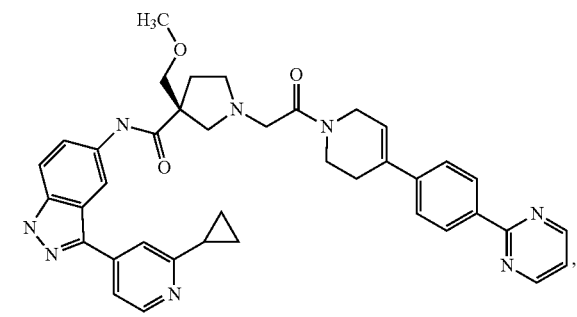
(A29)
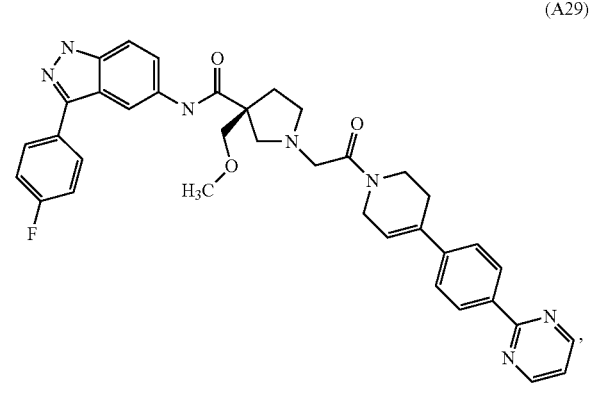
(A30)
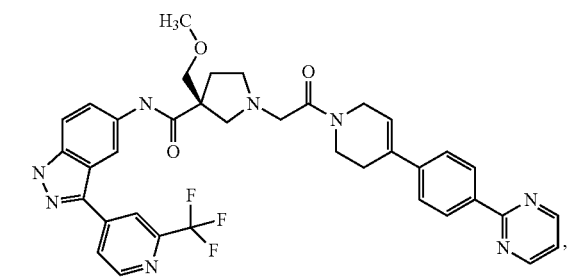
(A31)
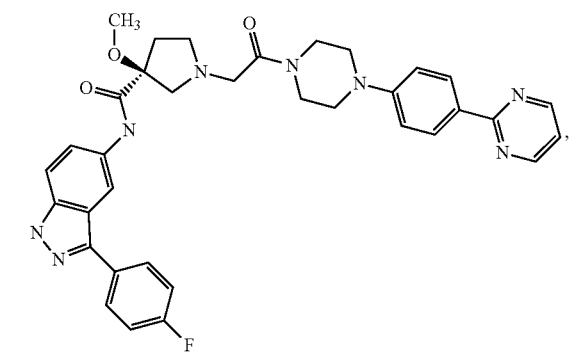

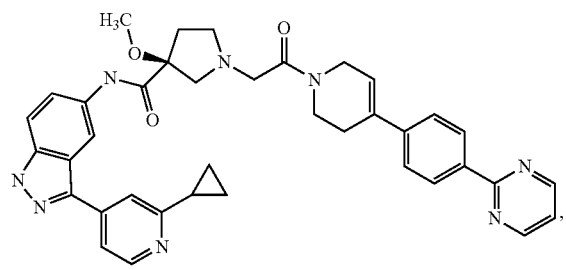
(A32)
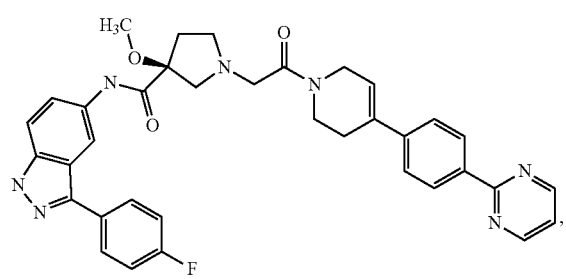
(A33)
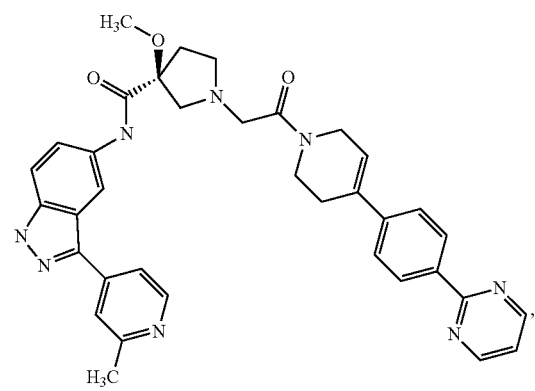
(A34)
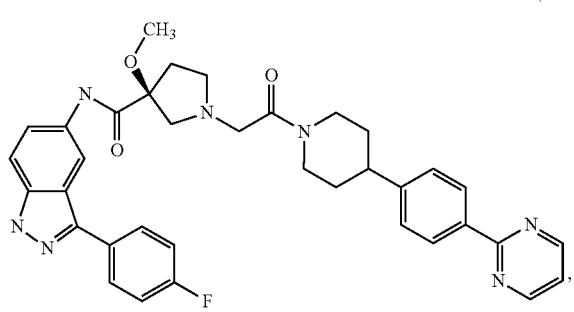
(A35)
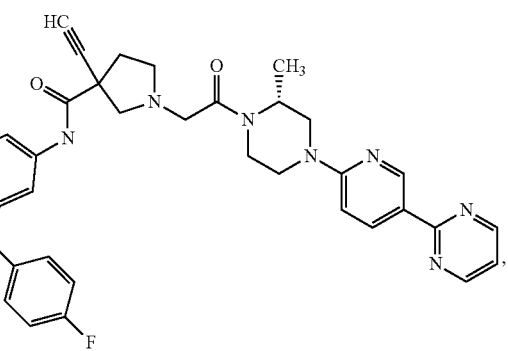
(A36)
(A37)
(A38)
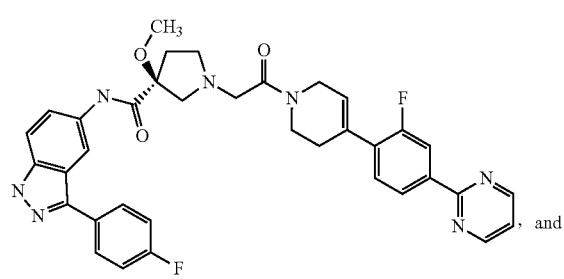
(A39)
and (A40)

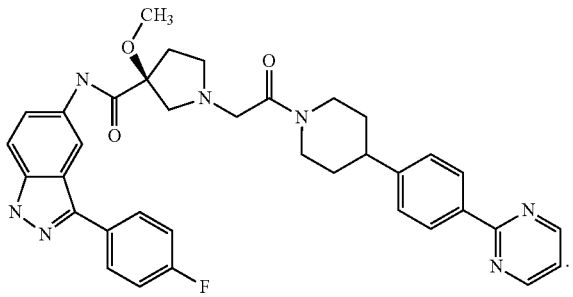

The present invention also includes methods (as discussed herein) for using any ERK inhibitor set forth in U.S. application Ser. No. 11/810,282; filed Jun. 5, 2007 or in U.S. provisional application No. 61/030,407; filed Feb. 21, 2008; each of which is herein incorporated by reference in its entirety. In an embodiment of the invention, the ERK inhibitor is any isolated antibody (e.g., monoclonal, recombinant, humanized, chimeric or polyclonal antibody) or antigen-binding fragment thereof that binds specifically to ERK1 and/or ERK2 and inhibits ERK activity.

Further Chemotherapeutic Agents

Further chemotherapeutic agents which may be administered in association with an ERK inhibitor include, e.g., one or more anti-neoplastic agents, e.g., including but not limited to one or more:
microtubule affecting agents;
alkylating agents;
antimetabolites;
natural products and their derivatives;
hormones and steroids (including synthetic analogs;
synthetics;
taxanes;
platinum coordinator compounds;
epidermal growth factor (EGF) inhibitors (e.g., antibodies or small molecules);
vascular endothelial growth factor (VEGF) inhibitors that are antibodies;
VEGF kinase inhibitors (e.g., antibodies or small molecules);
estrogen receptor antagonists or selective estrogen receptor modulators (SERMs);
anti-tumor nucleoside derivatives;
epothilones;
topoisomerase inhibitors;
vinca alkaloids;
antibodies that are inhibitors of αVβ3 integrins;
folate antagonists;
ribonucleotide reductase inhibitors;
anthracyclines;
biologics;
inhibitors of angiogenesis;
suppressors of tumor necrosis factor alpha (TNF-alpha);
Bcr/abl kinase inhibitors;
MEK1 and/or MEK 2 inhibitors (e.g., antibodies or small molecules);
IGF-1 and IGF-2 inhibitors (e.g., antibodies or small molecules);
inhibitors of RAF and BRAF kinases (e.g., antibodies or small molecules);
inhibitors of cell cycle dependent kinases such as CDK1, CDK2, CDK4 and CDK6 (e.g.,
antibodies or small molecules);
alkylating agents; or
farnesyl protein transferase inhibitors.

For example, in an embodiment of the invention, a further chemotherapeutic agent is one or more of the following: nitrogen mustards, ethylenimine derivatives, alkyl sulfonates, nitrosoureas, triazenes, Uracil mustard, Chlormethine, Cyclophosphamide, Ifosfamide, Melphalan, Chlorambucil, Pipobroman, Triethylene-melamine, Triethylenethiophosphoramine, Busulfan, Carmustine, Lomustine, Streptozocin, Dacarbazine, Temozolomide, folic acid antagonists, pyrimidine analogs, purine analogs and adenosine deaminase inhibitors, Methotrexate, 5-Fluorouracil, Floxuridine, Cytarabine, 6-Mercaptopurine, 6-Thioguanine, Fludarabine phosphate, Pentostatine, Gemcitabine, vinca alkaloids, anti-tumor antibiotics, enzymes, lymphokines and epipodophyllotoxins, Vinblastine, Vincristine, Vindesine, Bleomycin, Dactinomycin, Daunorubicin, Doxorubicin, Epirubicin, Idarubicin, Paclitaxel, taxotere, Mithramycin, Deoxyco-formycin, Mitomycin-C, L-Asparaginase, Interferons (e.g., IFN-alpha 2a or IFN-alpha 2b), Etoposide, Teniposide, synthetic analogs of steroids, 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex, inorganic platinum complexes, platinum coordination complexes, Cisplatin, Carboplatin, Hydroxyurea, Amsacrine, Procarbazine, Mitotane, Mitoxantrone, Levamisole, Hexamethylmelamine, Navelbene, CPT-11, Anastrazole, Letrazole, Capecitabine, Reloxafine, Droloxafine, Allocolchicine (NSC 406042), Halichondrin B (NSC 609395), Colchicine (NSC 757), Colchicine derivatives, NSC 33410, Dolastatin 10 (NSC 376128), Maytansine (NSC 153858), Rhizoxin (NSC 332598), Thiocolchicine (NSC 361792), Trityl Cysteine (NSC 83265), Vinblastine Sulfate (NSC 49842), Vincristine Sulfate (NSC 67574), Epothilone A, Epothilone, Discodermolide, Estramustine, Nocodazole, MAP4, oxaliplatin; trastuzumab, Cetuximab, EMD 72000 (Merck KGaA), anti-EFGR monoclonal antibody ABX, TheraCIM-h-R3, monoclonal antibody 425, monoclonal antibody ICR-62; Herzyme, PKI 166, EKB 569, GW 572016, CI-1033, trastuzumab-maytansinoid conjugate, mitumomab or Melvax II, erlotinib, gefitinib, bevacizumab, IMC-1C11, DC 101, semaxanib, SU 6688, tamoxifen, idoxifene, raloxifene, trans-2,3-dihydroraloxifene, levormeloxifene, droloxifene, MDL 103,323, acolbifene, 5-fluorouracil, gemcitabine, capecitabine, cytarabine (Ara-C), fludarabine (F-Ara-A), decitabine, chlorodeoxyadenosine (Cda, 2-Cda), BMS-247550, EPO906, topotecan, camptothecin; navelbine, vinblastine, antibodies that are inhibitors of αVβ3 integrins, LM-609, Methotrexate (MTX), Premetrexed (Alimta); Hydroxyurea (HU); Daunorubicin, Doxorubicin, Idarubicin, Rituximab, thalidomide, Gleevec (STI-571), AMN-17, ONO12380, SU11248 (Sunitinib), BMS-354825, PD0325901 and Arry-142886, NVP-AEW541, BAY 43-9006 (Sorafenib); CYC202, BMS387032, Flavopiridol; temozolomide; lonafarnib, tipifarnib or

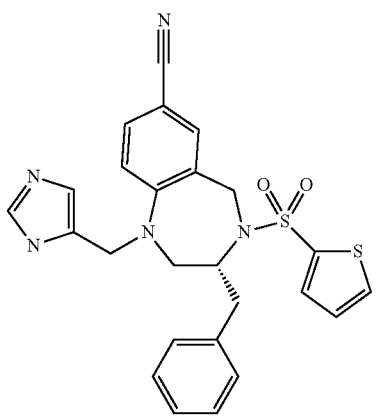 [SMILES: N#Cc1ccc2c(c1)CN(S(=O)(=O)c1cccs1)[C@H](Cc1ccccc1)CN2Cc1cnc[nH]1]

Furthermore any of the foregoing anti-cancer agents may be administered to a subject in the absence of any other drug, e.g., ERK inhibitor, and its effect on the subject to whom it is administered can be evaluated by determining IL-8 levels in the subject, e.g., as discussed herein.

Assays

The present invention provides a method for monitoring the effect of an anti-cancer agent, e.g., an ERK inhibitor, on tumor volume and/or blood cancer status and/or ERK pathway activation level, in the body of a subject suffering from a tumor or blood cancer which subject is administered said anti-cancer agent, comprising evaluating IL-8 levels in the body of the subject over time; wherein rising IL-8 levels indicate that tumor volume is increasing or that the blood cancer is progressing or that ERK pathway levels are rising; and falling IL-8 levels indicate that tumor volume is decreasing or that the blood cancer is diminishing or that ERK pathway levels are decreasing. Static levels of IL-8 indicate that the tumor volume or blood cancer status is static or that ERK pathway levels are static.

The mean normal level of IL-8 in the blood of a healthy patient is about 9 pg/ml whereas cancer patients, e.g., melanoma patients (stage II or III), exhibit elevated IL-8 levels, an average of about 123 pg/ml.

In an embodiment of the invention, reduction of IL-8 levels in response to treatment with an anti-cancer agent, e.g., ERK inhibitor, to any significant degree whatsoever, would indicate that tumor size is also decreasing (e.g., 1%, 2%, 3%, 5%, 10%, 20%, 25%, 50%, 75%, 90% or 93%). In an embodiment of the invention, Il-8 drops from an elevated level to a normal level. A qualitative assessment of whether a drop in IL-8, in response to an anti-cancer agent, e.g., an ERK inhibitor treatment, by e.g., a treating physician or clinician, can also be done so as to assess whether tumor growth and/or survival is being inhibited sufficiently-methods including such embodiments are within the scope of the present invention. In the expert, experienced judgment of the physician or clinician, an assessment as to whether the drop was sufficient and indicative of tumor inhibition can be made.

Blood cancers include leukemia and other conditions discussed herein. A blood cancer status diminishes or progresses with respect to its signs and/or symptoms and/or underlying physiological and/or biological causes.

IL-8 levels can be, in an embodiment of the invention, determined in, for example, the blood or serum or plasma or any other appropriate bodily fluid of a subject or in tumor tissue.

The present invention also provides a method for determining tumor volume or a change in tumor volume or blood cancer status or the activation level of the ERK pathway in a subject; comprising determining IL-8 levels in said subject (e.g., over time, e.g., in several measurements of IL-8); wherein rising IL-8 levels, in the subject, indicate rising tumor volume or ERK pathway activation or blood cancer progression; or that the anti-cancer agent (that was administered to the subject) is not preventing tumor volume increases or blood cancer progression or ERK pathway activation; and wherein decreasing IL-8 levels, in the subject, indicate decreasing tumor volume or ERK pathway activation or blood cancer regression or that the anti-cancer agent is preventing tumor volume increases or ERK pathway activation or blood cancer progression; and wherein steady IL-8 levels indicate steady tumor volume or ERK pathway activation or blood cancer status or that the anti-cancer agent is maintaining tumor volume or blood cancer status.

Such a method can be coupled with administration of an anti-cancer agent, such as an ERK inhibitor, and, then, evaluation of tumor volume or ERK pathway activation or blood cancer status as discussed above. Such a method serves to determine the effect of said agent on the tumor volume or blood cancer status. In an embodiment of the invention, such a method comprises the steps:

(i) measuring an IL-8 level in the body of said subject;
(ii) administering one or more doses of said anti-cancer agent, e.g., ERK inhibitor to said subject;
(iii) measuring an IL-8 level in the body of said subject following said administration; and
(iv) comparing the level of IL-8 measured in step (i) with the level of IL-8 measured in step (iii); wherein the anti-cancer agent is determined to inhibit tumor volume increase or blood cancer progression or ERK pathway activation if IL-8 levels are observed to decrease over time following said administration; or wherein the anti-cancer agent is determined not to inhibit tumor volume increase or blood cancer progression or ERK pathway activation if IL-8 levels are not observed to decrease over time following said administration. If the anti-cancer agent is determined to be satisfactory regarding inhibition of the tumor or blood cancer or ERK pathway activation, then, optionally, the clinician can elect to continue treatment with the agent. If the agent is not determined to be satisfactory, the clinician can elect to discontinue treatment or, alternatively, alter the agent's dosage (e.g., increase dosage) and, then, re-evaluate the effect of the agent.

The methods for monitoring the effect of an anti-cancer agent, e.g., an ERK inhibitor, can be applied, for example, in a method for determining if a subject has a medical condition (e.g., a medical condition mediated by expression and/or activity of ERK1 and/or ERK2) that is responsive to an anti-cancer agent, e.g., ERK inhibitor. For example, in such an embodiment of the invention, the subject's IL-8 levels are assayed during the course of anti-cancer agent treatment (as discussed herein); and the condition is determined to be unresponsive to said agent if the IL-8 levels are not observed to decrease over time following administration of said agent; or wherein the condition is determined to be responsive to said agent if the IL-8 levels are observed to decrease over time following administration of said agent. For example, in an embodiment of the invention, the method comprises:

(i) measuring an IL-8 level in the body of said subject;
(ii) administering one or more doses of said anti-cancer agent to said subject;
(iii) measuring an IL-8 level in the body of said subject following said administration;

(iv) comparing the level of IL-8 measured in step (i) with the level of IL-8 measured in step (iii); wherein said condition is determined to be unresponsive to said agent if the IL-8 levels are not observed to decrease over time following said administration; or wherein the condition is determined to be responsive to said agent if the IL-8 levels are observed to decrease over time following said administration. Optionally, a treating clinician can elect to initiate or continue treatment if the tumor or blood cancer is responsive to the anti-cancer agent. The clinician can opt to discontinue or forego treatment with the anti-cancer agent if the tumor or blood cancer is non-responsive to the agent.

The methods for monitoring the effect of anti-cancer agents, e.g., ERK inhibitors, may also be used in a method for evaluating dosage of the anti-cancer agent comprising monitoring the effect of the agent by the method set forth above; wherein the dosage is determined to be sufficient if the IL-8 level is observed to decrease over time following administration of a dose of the agent; or, wherein the dosage is determined to be insufficient if the IL-8 level is observed to increase over time or remain constant following a dose of the agent. For example, in an embodiment of the invention, the method comprises:
(i) measuring an IL-8 level in the body of said subject;
(ii) administering one or more doses of said anti-cancer agent, e.g., ERK inhibitor, to said subject;
(iii) measuring an IL-8 level in the body of said subject following said administration;
(iv) comparing the level of IL-8 measured in step (i) with the level of IL-8 measured in step (iii); wherein the dosage is determined to be sufficient if the IL-8 level is observed to decrease over time following administration of a dose of the agent or wherein the dosage is determined to be insufficient if the IL-8 level is observed to increase over time or remain constant following a dose of the agent. Optionally, the treating clinician can opt to increase dosage if the dosage is determined to be insufficient; or, to maintain dosage if the dose evaluated is determined to be effective.

In addition, the method for monitoring the effect of an anti-cancer agent, e.g., an ERK inhibitor, can be applied in a method for treating a tumor or blood cancer in a subject. Such a method comprises administering a dosage of anti-cancer agent, e.g., ERK inhibitor, to the subject and monitoring the effect of the anti-cancer agent by the monitoring method discussed above; and increasing the dosage of the anti-cancer agent if the IL-8 levels are determined to increase over time or remain constant following a dosage of the agent or maintaining dosage if IL-8 levels are determined to decrease over time. For example, an embodiment of the invention includes the steps:
(i) measuring an IL-8 level in the body of said subject;
(ii) administering one or more doses of the anti-cancer agent to said subject;
(iii) measuring an IL-8 level in the body of said subject following said administration; and
(iv) comparing the level of IL-8 measured in step (i) with the level of IL-8 measured in step (iii); and increasing the dosage of the agent if the IL-8 levels are determined to increase over time or remain constant following a dosage of the inhibitor, or maintaining dosage if IL-8 levels are determined to decrease over time.

The effect of an anti-cancer agent, e.g., an ERK inhibitor, can be evaluated at the outset of or in the midst of a treatment regimen. Specifically, in connection with any of the methods set forth above, the subject may have been administered one or more doses of anti-cancer agent, e.g., ERK inhibitor, before an initial measurement of IL-8, for example, prior to step (i) in the methods set forth above. In such an embodiment, IL-8 levels are determined during the course of an already initiated treatment regimen. In another embodiment of the invention, the dose is an initial, first dose in a treatment regimen—the subject has not been administered any previous doses in the regimen.

In an embodiment of the invention, a subject administered an anti-cancer agent, in connection with any of the methods discussed herein, which is an ERK inhibitor, is suffering from a tumor or blood cancer that is mediated by ERK1 and/or ERK2 expression and/or activity.

B-RAF and N-RAS

In an embodiment of the invention, a subject to be administered an ERK inhibitor and to be evaluated using an IL-8 biomarker, as discussed in detail herein, is also evaluated (e.g., before any ERK inhibitor treatment or IL-8 biomarker evaluation) for the possession of a mutant allele of B-RAF and/or N-RAS. If the subject has the mutant allele of B-RAF and/or N-RAS, treatment and/or evaluation of the IL-8 biomarker would proceed. In an embodiment of the invention, the N-RAS mutant allele determined is Q61R. In an embodiment of the invention, the B-RAF mutant allele determined is V600E and/or V600D. Evaluation of B-RAF mutations in a subject to be administered an ERK inhibitor is discussed in U.S. provisional application No. 60/991,351; filed Nov. 30, 2007, and in U.S. provisional application No. 61/034,615; filed Mar. 7, 2008; each of which is incorporated herein by reference in its entirety.

The BRAF genotype status of a cell (homozygous V600E BRAF or heterozygous V600E BRAF or homozygous V600D BRAF or heterozygous V600D BRAF or any BRAF genotype characterized by a gain-of-function phenotype) is also a predictive biomarker for ERK inhibitor sensitivity.

In an embodiment of the invention, B-RAF and/or N-RAS mutation status is evaluated in the cells of the tumor in the subject (e.g., melanoma cells).

Biomarkers and Methods of Treatment

The present invention provides methods for quickly and conveniently evaluating various aspects of a given anti-cancer agent, e.g., ERK inhibitor, therapeutic regimen In an embodiment of the invention, an ERK inhibitor is administered to a patient at a "therapeutically effective dosage" or "therapeutically effective amount" which preferably inhibits a disease or condition (e.g., tumor growth) to any extent. As discussed herein, the dosage can be adjusted according to observations made by the clinician, physician or veterinarian based, at least in part, on the behavior of IL-8 levels in the body of the subject during a course of anti-cancer agent treatment. For example, as a starting point, a dosage of an ERK inhibitor of the present invention can be about, e.g., 50 to about 400 mg once per day, e.g., about 50 to about 300 mg once per day, e.g., about 50 to about 350 mg twice a day, e.g., about 50 mg to about 200 mg twice a day, e.g., about 75 mg to about 125 mg administered twice a day e.g., about 100 mg administered twice a day.

The anti-cancer agents, e.g., ERK inhibitors, of this invention can be administered e.g., orally, e.g., as a solid dosage form, and in one embodiment as a capsule, and while the total therapeutically effective daily dose can be administered in one to four, or one to two divided doses per day, the therapeutically effective dose can, in an embodiment of the invention, be given once or twice a day, and, in one embodiment, twice a day.

In an embodiment of the invention, a "therapeutically effective dosage" of a chemotherapeutic agent or anti-cancer agent is, whenever possible, as set forth in the *Physicians' Desk Reference* 2003 (Thomson Healthcare; 57th edition (Nov. 1, 2002)) which is herein incorporated by reference Examples of cancers which may be treated by the methods of this invention include, but are not limited to:
(A) lung cancer (e.g., lung adenocarcinoma and non small cell lung cancer),
(B) pancreatic cancers (e.g., pancreatic carcinoma such as, for example, exocrine pancreatic carcinoma),
(C) colon cancers (e.g., colorectal carcinomas, such as, for example, colon adenocarcinoma and colon adenoma),
(D) myeloid leukemias (for example, acute myelogenous leukemia (AML), CML, and CMML),
(E) thyroid cancer,
(F) myelodysplastic syndrome (MDS),
(G) bladder carcinoma,
(H) epidermal carcinoma,
(I) melanoma (including superficial spreading melanoma (SSM), nodular melanoma, acral lentiginous melanoma or lentigo maligna),
(J) breast cancer,
(K) prostate cancer,
(L) head and neck cancers (e.g., squamous cell cancer of the head and neck),
(M) ovarian cancer,
(N) brain cancers (e.g., gliomas, such as glioma blastoma multiforme),
(O) cancers of mesenchymal origin (e.g., fibrosarcomas and rhabdomyosarcomas),
(P) sarcomas,
(Q) tetracarcinomas,
(R) neuroblastomas,
(S) kidney carcinomas,
(T) hepatomas,
(U) non-Hodgkin's lymphoma,
(V) multiple myeloma, and
(W) anaplastic thyroid carcinoma.

A physician or clinician can, optionally, also adjust the dosage of an anti-cancer agent, e.g., ERK inhibitor, using conventional techniques and clinical indicia in addition to IL-8 levels as discussed herein; such additional techniques and indicia are discussed below. For example, a clinician can evaluate the actual size and progress of the tumor being treated. The size and progress of a tumor can also be easily determined, for example, by X-ray, magnetic resonance imaging (MRI) or visually in a surgical procedure. In general, tumor size and proliferation can be measured by use of a thymidine PET scan (see e.g., Wells et al., Clin. Oncol. 8: 7-14 (1996)). Generally, the thymidine PET scan includes the injection of a radioactive tracer, such as [2-$^{11}$C]-thymidine, followed by a PET scan of the patient's body (Vander Borght et al., Gastroenterology 101: 794-799, 1991; Vander Borght et al., J. Radiat. Appl. Instrum. Part A, 42: 103-104 (1991)). Other tracers that can be used include [$^{18}$F]-FDG (18-fluorodeoxyglucose), [$^{124}$I]IUdR (5-[124I]iodo-2'-deoxyuridine), [$^{76}$Br]BrdUrd (Bromodeoxyuridine), [$^{18}$F]FLT (3'-deoxy-3' fluorothymidine) or [$^{11}$C]FMAU (2'-fluoro-5-methyl-1-β-D-arabinofuranosyluracil).

For example, melanoma progress can be monitored, by the physician or veterinarian by a variety of methods, and the dosing regimen can be altered accordingly. Methods by which to monitor melanoma include, for example, by patient interview or by physical examination (e.g., visual inspection and documentation of any lesion's size, shape or other visual qualities).

For example, neuroblastoma progress can also be monitored, by a physician or veterinarian, by a variety of methods, and the dosing regimen can be altered accordingly. Methods by which to monitor neuroblastoma include, for example, CT scan (e.g., to monitor tumor size), MRI scan (e.g., to monitor tumor size), chest X-ray (e.g., to monitor tumor size), bone scan, bone marrow biopsy (e.g., to check for metastasis to the bone marrow), hormone tests (levels of hormones like epinephrine), complete blood test (CBC) (e.g., to test for anemia or other abnormality), testing for catecholamines (a neuroblastoma tumor marker) in the urine or blood, a 24 hour urine test for check for homovanillic acid (HMA) or vanillyl mandelic acid (VMA) levels (neuroblastoma markers) and an MIBG scan (scan for injected I$^{123}$-labeled metaiodobetaguanidine; e.g., to monitor adrenal tumors).

For example, pancreatic cancer progress can also be monitored, by the physician or veterinarian, by a variety of methods, and the dosing regimen can be altered accordingly. Methods by which to monitor pancreatic cancer include blood tests to check for tumor markers CA 19-9 and/or carcinoembryonic antigen (CEA), an upper GI series (e.g., a barium swallow), endoscopic ultrasonography; endoscopic retrograde cholangiopancreatography (an X-ray of the pancreatic duct and bile ducts); percutaneous transhepatic cholangiography (an X-ray of the bile duct), abdominal ultrasound imaging or abdominal computer tomography scan (CT).

For example, breast cancer progress can also be monitored, by the physician or veterinarian, by a variety of methods, and the dosing regimen can be altered accordingly. Methods by which to monitor breast cancer include mammography, aspiration or needle biopsy or palpation.

For example, colorectal cancer progress can also be monitored, by the physician or veterinarian, by a variety of methods, and the dosing regimen can be altered accordingly. Methods by which to monitor colorectal cancer include computer tomography scan (CT), MRI scan, chest X-ray, PET scan, fecal occult blood tests (FOBTs), flexible proctosigmoidoscopy, total colonoscopy, and barium enema.

For example, bladder cancer progress can also be monitored, by the physician or veterinarian, by a variety of methods, and the dosing regimen can be altered accordingly. Methods by which to monitor bladder cancer include urinalysis to detect elevated levels of tumor markers (e.g., nuclear matrix protein (NMP22)) in the urine, urinalysis to detect microscopic hematuria, urine cytology to detect cancer cells by examining cells flushed from the bladder during urination, bladder cystoscopy, intravenous pyelogram (IVP), retrograde pyelography, chest X-ray to detect metastasis, computed tomography (CT), bone scan, MRI scan, PET scan or biopsy.

For example, lung cancer progress can also be monitored, by the physician or veterinarian, by a variety of methods, and the dosing regimen can be altered accordingly. Methods by which to monitor lung cancer include chest X-ray, CT scan, low-dose helical CT scan (or spiral CT scan), MRI scan, PET scan, bone scan, sputum cytology, bronchoscopy, mediastinoscopy, biopsy (e.g., needle or surgical), thoracentesis or blood tests to detect PTH (parathyroid hormone), CEA (carcinogenic antigen) or CYFRA21-1 (cytokeratin fragment 19).

For example, prostate cancer progress can also be monitored, by the physician or veterinarian, by a variety of methods, and the dosing regimen can be altered accordingly. Methods by which to monitor prostate cancer include digital rectal examination, transrectal ultrasound, blood tests taken to check the levels of prostate specific antigen (PSA) and prostatic acid phosphatase (PAP), biopsy, bone scan and CT scan.

Diagnostics and Patient Selection

The present invention provides a method for diagnosing the presence of a tumor or blood cancer in a patient. The diagnostic method comprises determining if the patient exhibits elevated levels of IL-8. If the patient is determined to exhibit elevated IL-8, then the patient is determined to suffer from the tumor or blood cancer. In an embodiment of the invention, the patient is further examined, with additional tests, for the presence of tumor or blood cancer if the IL-8 levels indicate such a presence. In an embodiment of the invention, the diagnosis of tumor or blood cancer in the patient as set forth above is confirmed, e.g., using conventional techniques. For example, the presence of a tumor can be confirmed by X-ray, MRI, CT scan, PET scan, palpation, ultrasonography or surgery. Blood cancer can be confirmed, e.g., using blood tests (e.g., a complete blood count (CBC)).

In an embodiment of the invention, diagnosis of the presence of tumor or blood cancer in a patient is followed by treatment with a therapeutically effective amount of an anti-cancer agent, e.g., an ERK inhibitor, or combination thereof with an additional anti-cancer therapeutic agent or anti-cancer procedure as set forth herein.

In an embodiment of the invention, the normal IL-8 level is as determined by western blots, immunohistochemistry, microscopy, ELISA (enzyme linked immuosorbent assay) or by radioimmunoassay (RIA). In an embodiment of the invention, IL-8 is measured in any suitable bodily fluid or tissue of the patient, for example, blood, plasma, serum or tumor tissue.

In an embodiment of the invention, supranormal IL-8 levels are above normal levels relative to the average person. Normal IL-8 levels in the population as well as elevated IL-8 levels in melanoma patients are discussed above. In another embodiment of the invention, supranormal levels are significantly above the non-cancerous, normal levels for the particular subject being evaluated. In an embodiment of the invention, supranormal levels are levels that are observed to increase consistently over time in a patient being evaluated. In such an embodiment a patient's IL-8 level is measured at an initial time point and measured at one or more points in the future. If one or more of the future measurements is significantly higher than a previous measurement, the patient is determined to exhibit an elevated or supranormal IL-8 level. In an embodiment of the invention, elevated or supranormal levels of IL-8 in a patient are any level that a practitioner of ordinary skill in the art would recognize as such. In an embodiment of the invention, an elevated or supranormal level of IL-8 is at least about 50% to about 100% (e.g., 50%, 55%, 60%, 65%, 70%, 75%, 80%, 85%, 90%, 95%, 100%, 200%, 300%, 400% or 500%) higher than a normal level.

The present invention provides further methods for using IL-8 biomarkers. In an embodiment of the invention, if cells of a tumor blood cancer express ERK1 and/or ERK2 and a subject with the tumor or cancer exhibits elevated IL-8 levels (e.g., in the patient's plasma), the tumor is likely to be responsive or sensitive to ERK inhibition. If the patient is identified to possess a tumor that expresses or if the tumor type is known to express ERK1 and/or ERK2 and if the patient exhibits elevated or supranormal IL-8 levels or possesses a tumor type known to be associated with elevated IL-8, then the patient is selected for treatment with an ERK inhibitor or the ERK inhibitor is selected for treatment of the patient's tumor, or the patient is identified as having a tumor likely sensitive to an ERK inhibitor—in such cases, optionally, the patient may then be treated with an ERK inhibitor.

Determination of IL-8 Levels

IL-8 levels may be measured by any of several methods which are very well known in the art; some of which are discussed infra.

IL-8, in a sample, can be quantitated, for example, by simply hiring or contracting with a commercial laboratory to perform the assay. Alternatively, the practitioner can perform the assay himself. In an embodiment of the invention, IL-8 is quantitated by a radioimmunoassay (RIA) (see e.g., Smith et al., J. Clin. Endocrin. Metab. 77(5): 1294-1299 (1993); Cohen et al., J. Clin. Endocrin. Metab. 76(4): 1031-1035 (1993); Dawczynski et al., Bone Marrow Transplant. 37:589-594 (2006); and Clemmons et al., J. Clin. Endocrin. Metab. 73:727-733 (1991)), western blot, microscopy, or by ELISA (enzyme linked immunosorbent assay). For example, in an embodiment of the invention, IL-8 in a sample of a patient's tumor tissue, plasma, blood or serum is quantitated.

In an embodiment of the invention, Western blots are performed as follows: A sample is electrophoresed on a poly-acrylamide-sodium dodecyl sulfate (SDS-PAGE) gel (e.g., 10, 12 or 14%) and transferred onto nitrocellulose or some other suitable membrane. The membrane is then incubated with a primary antibody which binds to the IL-8 protein being evaluated, optionally washed at least once and then incubated with a detectably labeled secondary antibody that binds to the primary antibody and optionally washed again at least once. The presence of the secondary antibody is then detected. For example, if the secondary antibody is labeled with a chemi-luminescence label, the membrane is exposed to film and then the film is developed. In an embodiment of the invention, each lane of the autoradiograph is scanned and analyzed by densitometer or analyzed visually.

In an embodiment of the invention, an ELISA assay employs an antibody specific for human IL-8 coated on a 96-well plate. Standards and samples are pipetted into the wells and IL-8 present in a sample is bound to the wells by the immobilized antibody. The wells are washed and biotinylated anti-IL-8 antibody is added. After washing away unbound biotinylated antibody, HRP-conjugated streptavidin is pipetted to the wells. The wells are again washed, a TMB substrate solution is added to the wells and color develops in proportion to the amount of IL-8 bound. The stop solution changes the color from blue to yellow, and the intensity of the color is measured at 450 nm. A standard ELISA curve using known concentrations of IL-8 can be plotted and the concentration of IL-8 in the unknown sample (e.g., the serum of a patient) can be determined by comparing the signal observed therein with the signal observed in the standard. Other ELISA formats which vary from this may also be employed.

ERK Pathway

The IL-8 biomarker can also be used as a biomarker for determining if an ERK inhibitor is inhibiting ERK (ERK1 and/or ERK2) pathway activity or activation. If the ERK pathway in malignant cells is inhibited by an ERK inhibitor, this indicates that the inhibitor is likely to be effective at reducing growth and/or survival and/or metastasis of the malignant cells. Effective pathway inhibition will, in turn, inhibit cell division of the targeted malignant cells. Studies using ERK inhibitor 2 demonstrated that, following treatment of a tumor with ERK inhibitor, the tumor size reduced and the surviving remnants of the tumor lacked detectable phospho-ERK.

The "ERK pathway" plays a central role in regulating mammalian cell growth by relaying extracellular signals from ligand-bound cell surface tyrosine kinase receptors such as members of the erbB family, PDGF, FGF, and VEGF receptor tyrosine kinase. Activation of the ERK pathway is via a cascade of phosphorylation events that includes activation of Ras. Activation of Ras leads to the recruitment and activation of Raf, a serine-threonine kinase. The RAF component of this pathway is a serine/threonine kinase and has three isoforms (BRAF, ARAF, and RAF1) that activate the MEK-ERK cascade. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation and, eventually, cell growth and division. The ERK signalling pathway has been extensively studied and is well known in the art.

EXAMPLES

The following information is provided for more clearly describing the present invention and should not be construed to limit the present invention. Any and all of the compositions and methods described below fall within the scope of the present invention.

Example 1

IL-8 Levels Correlate with ERK Inhibition

Il-8 levels in LOX xenograft mice and A375-SM xenograft mice administered ERK inhibitor 2 (structure set forth herein) were measured and correlated to tumor size (Table 1). LOX and A375-SM cells are a human melanoma cell lines derived from lymph node metastasis of patients with malignant melanoma. In these experiments, IL-8 was found to positively correlate with tumor size and to respond, with tumor size, to ERK inhibitor treatment. Various B-RAF mutant melanoma cell lines were also analyzed and determined to express high levels of IL-8; some non-melanoma lines were also analyzed and shown to have very low levels of IL-8 (Table 2)

LOX Xenograft Preparation Procedure
1. Inoculated mice with $0.5 \times 10^6$ LOX melanoma cells in the right flank, subcutaneously, in Matrigel (100 µl).
2. When tumor volumes were approximately 120 mm$^3$, mice were grouped (n=10) for treatment.
3. ERK inhibitor #2 at a dose of 20, 40, or 60 mpk (milligrams per kilogram of body weight) was administered P.O., BID (200 µl) prepared in 20% hydroxyl-propyl-β-cyclodextrin (20% HPBCD).
4. Measured tumor volumes twice a week for 28 days.
5. At the end of the experiment, harvested tumors and plasma of the animals. Cut a section from each tumor and fixed in formalin for immunohistochemical analysis. Snap-froze the remaining tumor and stored at −80° C.

Daily Preparation of ERK Inhibitor #2 for LOX Xenograft Animal Dosing
Average mouse body weight was 19.4 grams.
1. Added 105 mg of ERK inhibitor #2 to 18 ml of 20% HPBCD. This was the 60 mpk dosing solution for groups 4 and 8. Vortexed well until drug went into solution.
2. Added 6 ml of 60 mpk ERK inhibitor #2 to 3 ml of 20% HPBCD. This was the 40 mpk dosing solution for groups 3 and 7.
3. Added 3 ml of 60 mpk ERK inhibitor #2 to 6 ml of 20% HPBCD. This was the 20 mpk dosing solution for groups 2 and 6.

Daily Preparation of Vehicle 20% HPBCD for LOX Xenograft Animal Dosing
Added 9 ml of 20% HPBCD to a separate tube for vehicle groups 1 and 5.

Monitoring of LOX Xenograft Animals
Tumor volumes and body weights were measured twice a week. The data showing reduction of IL-8 with increasing amounts of drug in LOX mouse xenografts models is shown in Table 3.

A375-SM Xenograft Preparation Procedure
1. Inoculated mice with $5 \times 10^6$ A375-SM melanoma cells in the right flank subcutaneously in Matrigel (100 µl).
2. When tumor volumes were approximately 102 mm$^3$, mice were grouped (n=10) for treatment.
3. ERK inhibitor 2 at a dose of 30, 40, or 50 mpk was administered P.O., BID (200 µl) prepared in 20% hydroxyl-propyl-β-cyclodextrin (20% HPBCD).
4. Measured tumor volumes twice a week for 28 days.
5. At the end of the experiment, harvested tumors and plasma of the animals. Cut a section from each tumor and fixed in formalin for immunohistochemical analysis. Snap-froze the remaining tumor and store at −80° C.

Daily Preparation of ERK Inhibitor #2 for A375-SM Xenografts
Average mouse body weight was 22 g.
1. Added 126.5 mg of ERK inhibitor #2 to 23 ml of 20% HPBCD. This was the 50 mpk dosing solution for groups 4 and 8. Vortexed well until drug went into solution.
2. Added 8 ml of 50 mpk ERK inhibitor #2 to 2 ml of 20% HPBCD. This was the 40 mpk dosing solution for groups 3 and 7.
3. Added 6 ml of 50 mpk ERK inhibitor #2 to 4 ml of 20% HPBCD. This was the 30 mpk dosing solution for groups 2 and 6.

Daily Preparation of Vehicle 20% HPBCD for A375-SM Xenografts
Added 9 ml of 20% HPBCD to a separate tube for vehicle groups 1 and 5.

Monitoring A375-SM Xenografts
Tumor volumes and body weights were measured twice a week. The data showing reduction of IL-8 with increasing amounts of drug in A375-SM mouse xenografts models is shown in Table 4.

Measuring IL-8 Levels in Mouse Plasma
Plasma was obtained from mice carrying human tumor xenografts and used undiluted in the assay. Bioplex Human IL-8 assay beads were obtained from Bio-Rad Laboratories (Hercules, Calif.). Bio-Plex assays contain dyed beads conjugated with monoclonal antibodies specific for a target protein or peptide such as a cytokine. The system uses polystyrene beads internally dyed with differing ratios of two spectrally distinct fluorophores. Each fluorophore can have any of 10 possible levels of fluorescent intensity, thereby creating a family of 100 spectrally addressed bead sets.

Each of the bead sets contain a capture antibody specific for a unique target protein. The antibody-conjugated beads are allowed to react with sample and a secondary, or detection, antibody in a microplate well to form a capture sandwich immunoassay. Multiplex assays are created by mixing bead sets with different conjugated antibodies to simultaneously test for many analytes in one sample.

The assay solution is drawn into the Bio-Plex array reader, which illuminates and reads the sample. When a red diode "classification" laser (635 nm) in the Bio-Plex array reader illuminates a dyed bead, the bead's fluorescent signature identifies it as a member of one of the 100 possible sets. Bio-Plex Manager software correlates each bead set to the assay reagent that has been coupled to it (for example, an IL-2 capture antibody coupled to bead #36). In this way the Bio-Plex system can distinguish between the different assays combined within a single microplate well. A green "reporter" laser (532 nm) in the array reader simultaneously excites a fluorescent reporter tag (phycoerythrin, or PE) bound to the detection antibody in the assay. The amount of green fluorescence is proportional to the amount of analyte captured in the immunoassay.

The assay was done according to the "Bio-Plex Cytokine Assay Instruction Manual". IL-8 standards were diluted in 4-fold dilution steps in mouse serum standard diluent from the Mouse serum diluent kit (Bio-Rad Laboratories; Hercules, Calif.). The concentrations for the standards ranged from the published value for each specific IL-8 kit to the lowest value in seven 4-fold steps. The dilutions were done for a narrow range curve starting at ~2300 pg/ml to 1 pg/ml. The machine was set to the High PMT setting. Each dilution was set up in duplicate.

A 96-well filter plate (Millipore; Billerica, Mass.) was used in the assay. 100 ul of Bio-Plex Assay buffer was put into each well and sucked through at 2" Hg pressure. The beads were added and then washed 2× with wash buffer sucking through each time as described above. 50 ul of samples (mouse plasma) and standards were added to the wells in duplicate and shaken at room temperature for 30 minutes. After 3 washes, detection antibody was added and incubated for another 30 minutes. The plate was washed again 3×. Streptavidin was added for 10 minutes and then washed off before resuspending the beads in Bioplex assay buffer and reading on the Bio-Plex instrument.

The data correlating IL-8 levels in ERK inhibitor-treated mice are set forth below in Tables 3 and 4.

Measuring IL-8 Levels in Tumor Cell Lines

Cells were plated at $4 \times 10^5$ cells per well in a 6 well dish. After 24 hours, the media was sucked off and spun down for 5 minutes at 1000 rpm in a 4° C. microfuge (or 3000 rpm in a table top centrifuge).

The assay was done according to the "Bio-Plex cytokine Assay Instruction Manual". IL-8 standards were diluted in 4-fold dilution steps in the cell culture medium in which the cells were grown. The concentrations for the standards range were ascertained from the published value for each specific IL-8 kit. The dilutions were done for a broad range curve starting at ~23000 pg/ml to 10 pg/ml. The machine was set to the Low PMT setting. Each dilution was set up in duplicate.

All other steps were done as described above. 50 ul of Growth medium (harvested from cells) were used per well.

| Bio-Plex materials | |
|---|---|
| Bio-Plex Cytokine Reagent Kit Bio-Rad | Wash Buffer Assay Buffer Detection antibody diluent Streptavidin |
| Bio-Plex Grp I IL-8 Assay Bio-Rad | Human Cytokine Standard Anti Human Grp I IL-8 Human Grp I IL-8 Detection Antibody |
| Bio-Plex Mouse Serum Diluent Bio-Rad | Mouse serum Standard Diluent Mouse serum Sample Diluent |

TABLE 1

IL-8 levels in LOX (human melanoma) xenograft mouse plasma vs. tumor size.

| Sample | IL-8 | Tumor Volume |
|---|---|---|
| UT SCID | 0.23 | 0 |
| #1 | 0.4 | 121 |
| #2 | 0.3 | 122 |
| #3 | 0.37 | 127 |
| #4 | 0.37 | 153 |
| #5 | 0.59 | 172 |
| #6 | 0.59 | 189 |
| #7 | 0.48 | 207 |
| #8 | 0.71 | 215 |
| #9 | 0.57 | 225 |
| #10 | 0.84 | 241 |
| #11 | 0.47 | 271 |
| #12 | 0.72 | 282 |
| #13 | 0.5 | 290 |
| #14 | 0.51 | 299 |
| #15 | 0.81 | 406 |
| #16 | 8.54* | 440 |
| #17 | 0.96 | 609 |
| #18 | 1.42 | 749 |
| #19 | 2.13 | 872 |
| #20 | 2.35 | 985 |
| #21 | 3.4 | 986 |
| #22 | 2.85 | 1189 |
| #23 | 4.45 | 1245 |
| #24 | 3.73 | 1276 |
| #25 | 2.99 | 1546 |
| #26 | 7.42 | 1712 |
| #27 | 4.5 | 1969 |

*Mouse #16 showed metastasis of the tumor to the gut; this may explain the high levels of IL-8 observed despite carrying only a medium sized tumor.
The "Sample" column indicates the mouse that corresponds to the data in the other columns. The "IL-8" column contains the concentration of IL-8 in each mouse's plasma (pg/ml). The "Tumor Volume" column indicates the tumor volume in each mouse ($mm^3$).

These data demonstrated that tumor volume directly correlated with IL-8 levels in the mice tested.

A linear regression analysis of these data (X=IL-8 levels, Y=tumor volume) yielded a line with the equation Y=291X+128 with an $R^2$ value of 0.84; and in one embodiment of the invention, a correlation between IL-8 plasma levels and tumor volume (e.g., melanoma tumor volume, e.g., for LOX cell mediated tumors) can be expressed by this equation.

TABLE 2

Elevated Expression of IL-8 Protein in Growth Medium of Human B-RAF Mutant Melanoma Cell Lines.

| Cell line | IL-8 pg/ml |
|---|---|
| A2058 | 31548 |
| LOX | 24413 |
| WM-115 | 14911 |
| WM-266-4 | 13896 |
| A375.SM | 13035 |
| COLO205 | 3 |
| A427 | 15 |

TABLE 3

IL-8 levels in LOX xenograft mouse plasma in mice administered inhibitor 2.

| Sample ID | Tumor Volume $mm^3$ | IL-8 pg/ml |
|---|---|---|
| Vehicle | 2382 | 10.33 |
| Vehicle | 1314 | 6.56 |
| Vehicle | 1027 | 4.33 |

TABLE 3-continued

IL-8 levels in LOX xenograft mouse plasma in mice administered inhibitor 2.

| Sample ID | Tumor Volume mm³ | IL-8 pg/ml |
|---|---|---|
| ERK inh #2-20 mpk | 897 | 2.23 |
| ERK inh #2-20 mpk | 1194 | 3.51 |
| ERK inh #2-20 mpk | 1361 | 3.25 |
| ERK inh #2-20 mpk | 597 | 2.78 |
| ERK inh #2-40 mpk | 91 | 0.2 |
| ERK inh #2-40 mpk | 43 | 0.04 |
| ERK inh #2-40 mpk | 88 | 0.15 |
| ERK inh #2-40 mpk | 49 | 0.05 |
| ERK inh #2-60 mpk | 21 | <0.04 |
| ERK inh #2-60 mpk | 15 | <0.04 |
| ERK inh #2-60 mpk | 26 | <0.04 |

TABLE 4

IL-8 levels in A375-SM xenograft mouse plasma in mice administered inhibitor 2.

| Sample ID | Tumor Volume mm³ | IL-8 pg/ml |
|---|---|---|
| Vehicle | 2865 | 2145 |
| Vehicle | 1765 | 1045 |
| Vehicle | 1662 | 844 |
| Vehicle | 965 | 361 |
| Vehicle | 1375 | 247 |
| ERK inh #2-30 mpk | 1247 | 366 |
| ERK inh #2-30 mpk | 1934 | 266 |
| ERK inh #2-30 mpk | 1486 | 226 |
| ERK inh #2-30 mpk | 1168 | 162 |
| ERK inh #2-40 mpk | 2263 | 206 |
| ERK inh #2-40 mpk | 800 | 168 |
| ERK inh #2-40 mpk | 1066 | 166 |
| ERK inh #2-40 mpk | 1208 | 150 |
| ERK inh #2-40 mpk | 606 | 73 |
| ERK inh #2-50 mpk | 488 | 41 |
| ERK inh #2-50 mpk | 232 | 24 |
| ERK inh #2-50 mpk | 226 | 20 |
| ERK inh #2-50 mpk | 218 | 17 |
| ERK inh #2-50 mpk | 101 | 13 |

Experiments were also performed wherein A2058 B-RAF mutant melanoma cells were treated with ERK inhibitor #1 (structure set forth herein), ERK inhibitor #2 (structure set forth herein), the PD MEK inhibitor

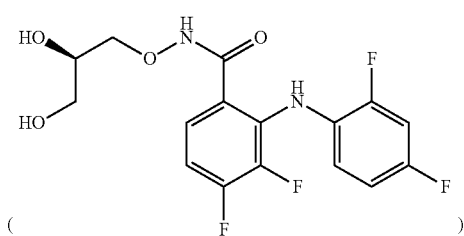 [SMILES: O=C(NOC[C@H](O)CO)c1ccc(F)c(F)c1Nc1ccc(F)cc1F]

or the AR MEK inhibitor

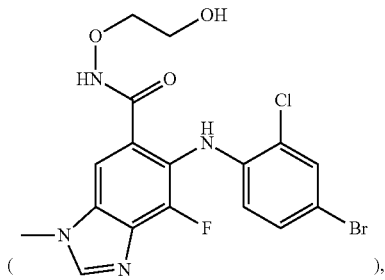 [SMILES: Cn1cnc2c(F)c(Nc3ccc(Br)cc3Cl)c(C(=O)NOCCO)cc21]

or DMSO as a negative-control, for 8 hours.

These experiments were performed using IL-8 ELISAs from R&D Systems (Minneapolis, Minn.). Approximately $1 \times 10^6$ A2058 cells were plated onto 10 cm dishes containing 10 ml of growth media. The following day, compound was added and allowed to incubate for 8 hours. The media was removed from the plates, diluted 32× and used in the ELISA. The data from these experiments are set forth below in Table 5.

TABLE 5

IL-8 levels in growth media of A2058 melanoma cells following exposure to ERK or MEK inhibitors.

| Inhibitor | IL-8 pg/ml |
|---|---|
| ERK inh #1 | 3392 |
| ERK inh #2 | 2208 |
| PD | 2080 |
| AR | 1632 |
| DMSO | 21024 |

These data demonstrated that IL-8 levels directly correlated with the level of inhibition of the MEK and/or ERK cellular pathways by added inhibitors.

Experiments were also performed wherein A2058 B-RAF mutant melanoma cells were treated with ERK inhibitor #1 for 8 hours and then compared with the parental A2058 cells using microarray technology. In this experiment, IL-8 gene expression (mRNA levels) was observed to drop 28-fold. These data also demonstrated that the levels of IL-8 mRNA expression directly correlated with the level of inhibition of ERK cellular pathways by added ERK inhibitor #1.

* * *

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. A method for determining if a subject with a malignant tumor or blood cancer has a malignant tumor or blood cancer that is responsive to an agent selected from the group consisting of:

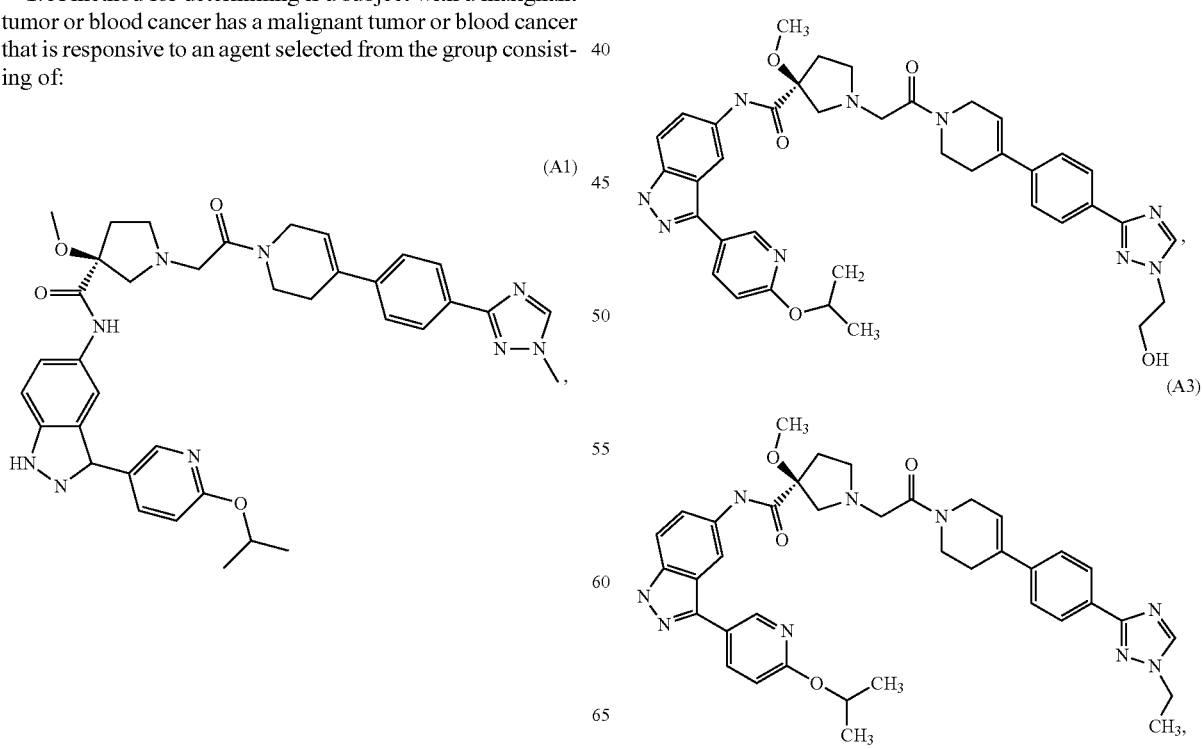

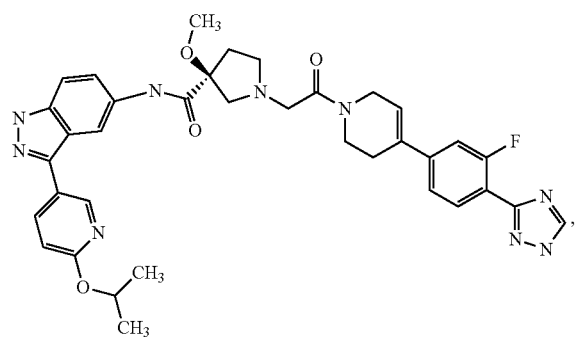
(A4)
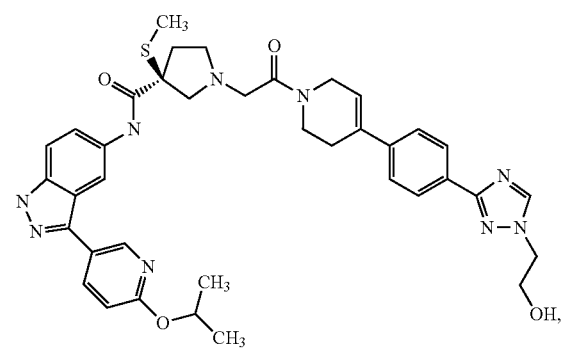
(A8)
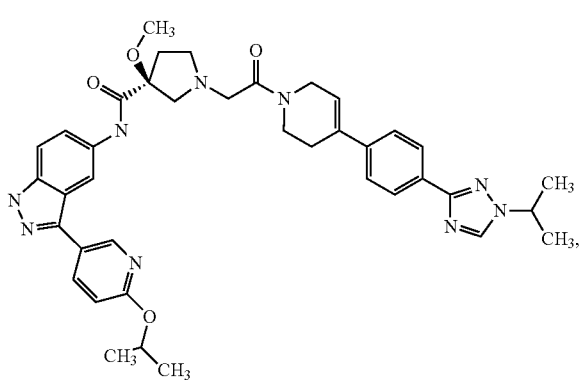
(A5)
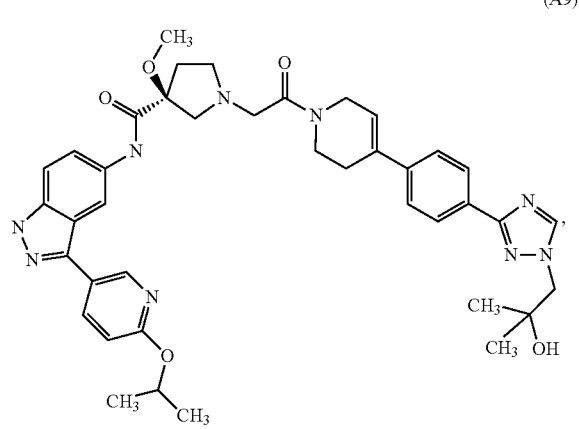
(A9)
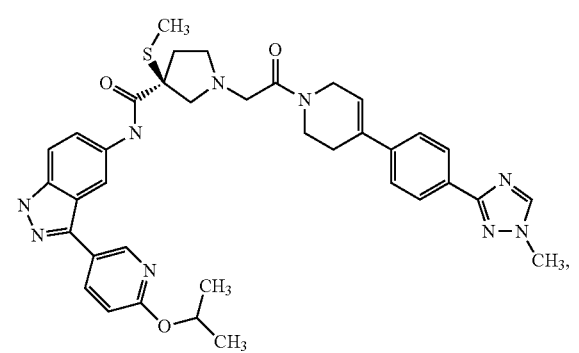
(A6)
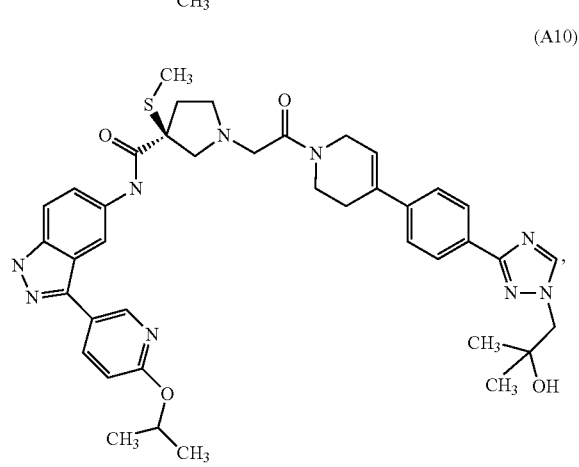
(A10)
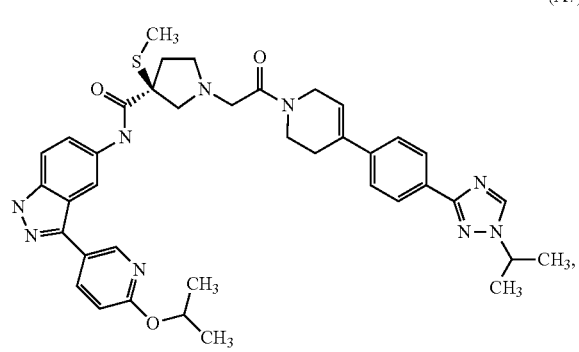
(A7)
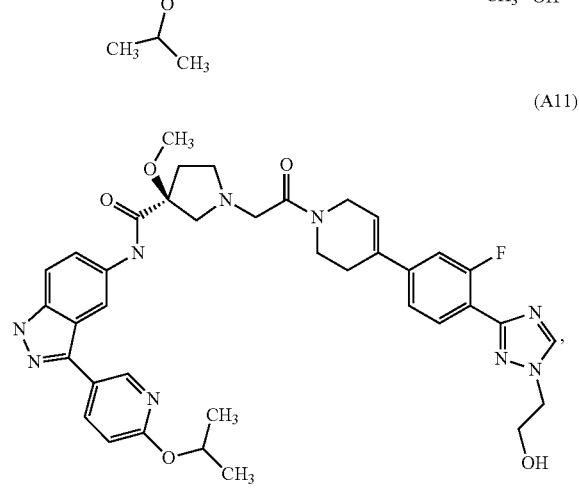
(A11)

-continued
(A12)
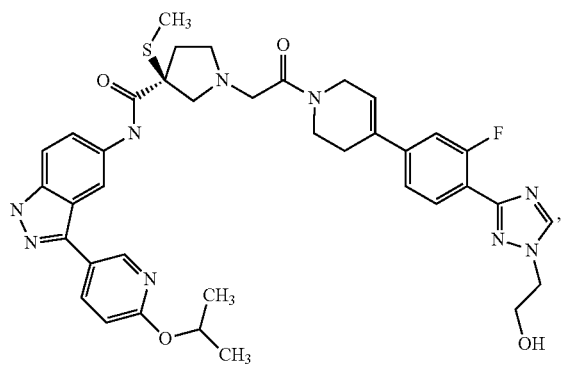
(A13)
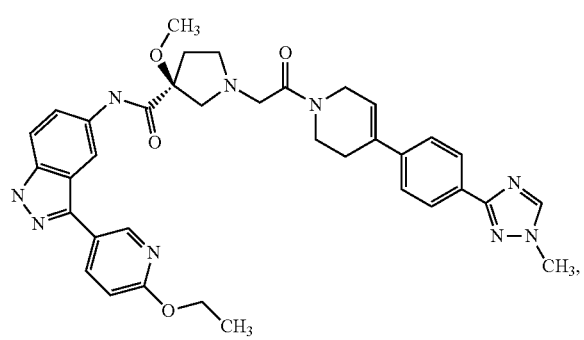
(A14)
(A15)
-continued
(A16)
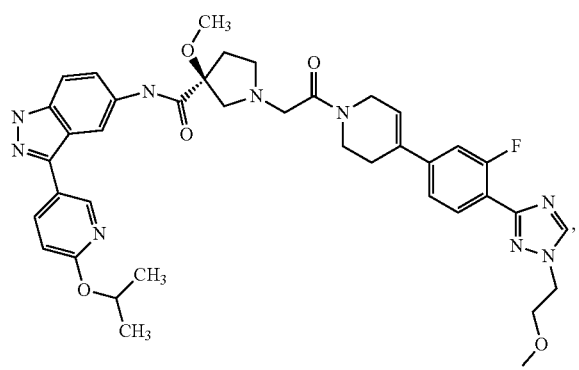
(A18)
(A20)
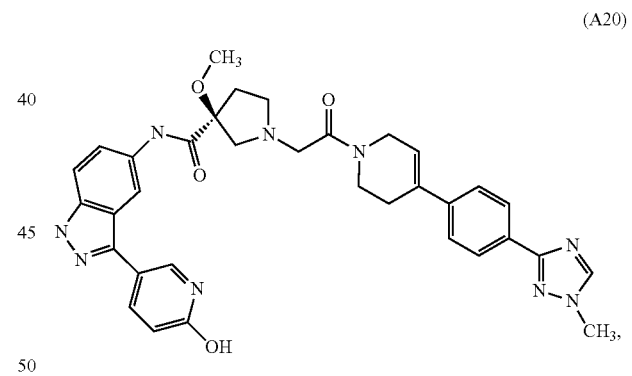
(A21)
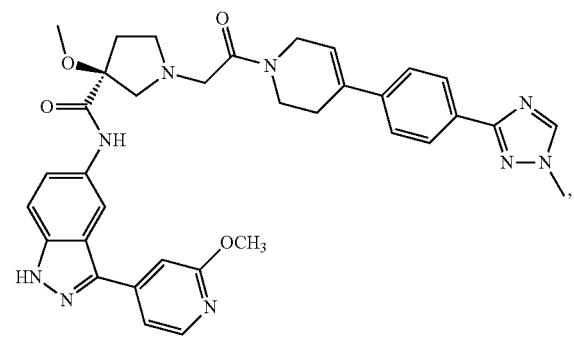

(A22) 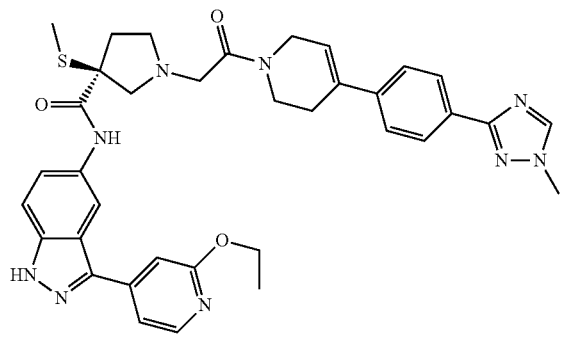
(A23) 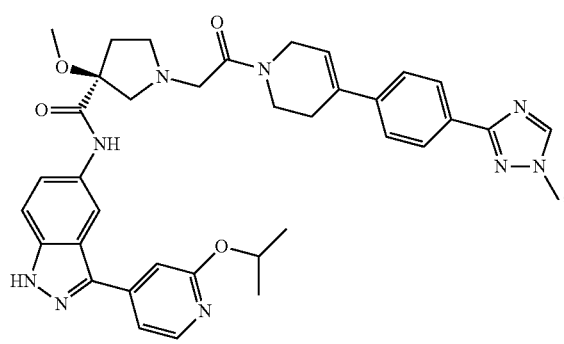
(A24) 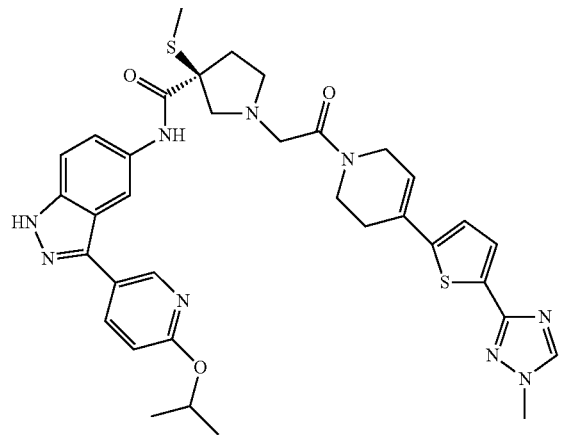
(A25)
(A26)
(A27)
(A28)
(A29) 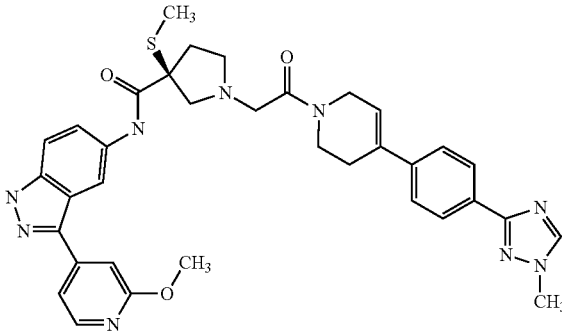
(A30) 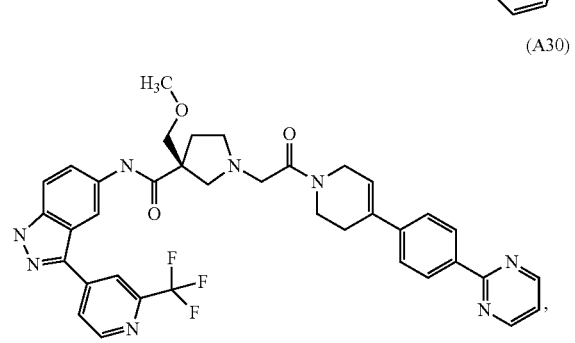

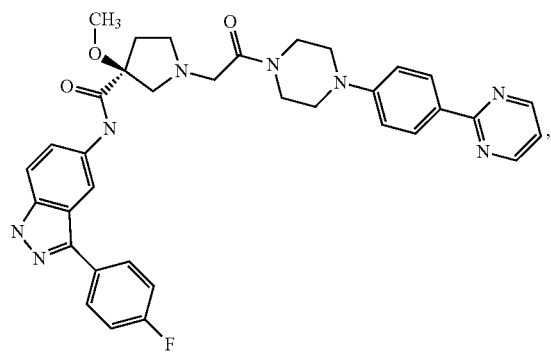
(A31)
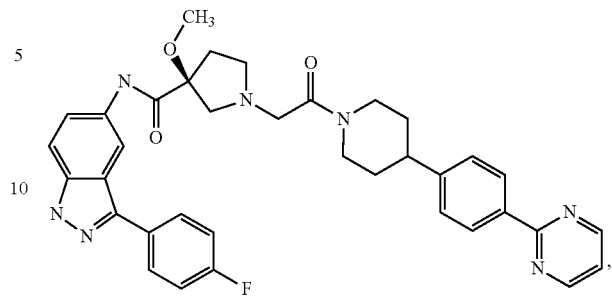
(A35)
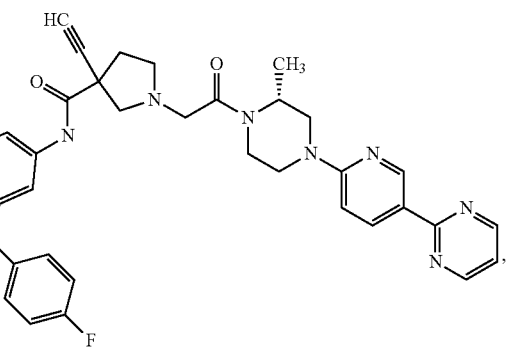
(A32), (A33), (A34)
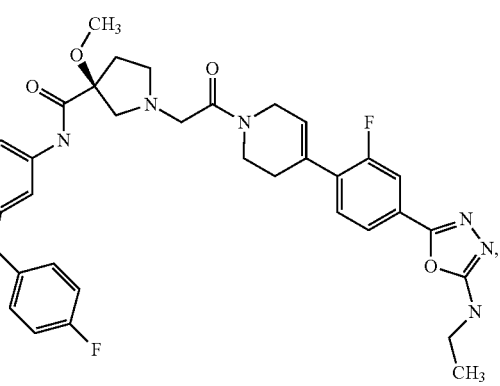
(A36), (A37)
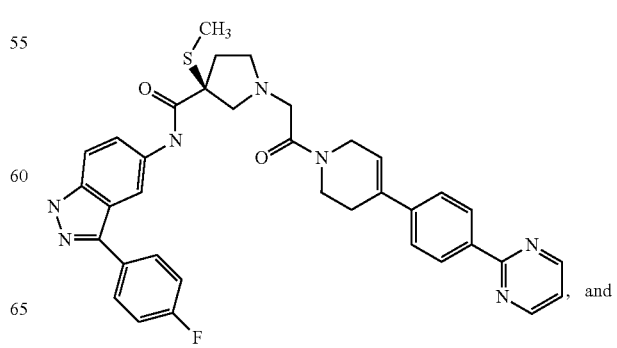
and -continued

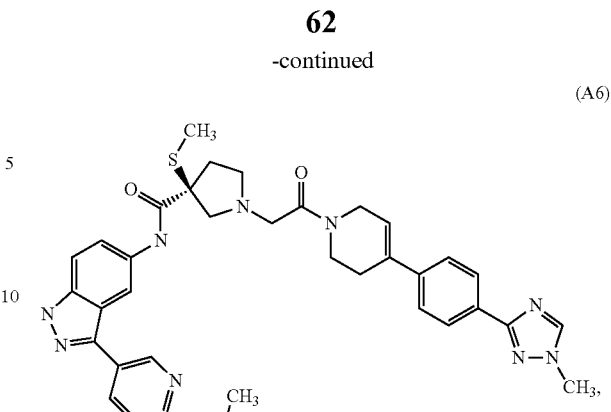

comprising determining an IL-8 level in the blood or serum of the subject, administering the agent to the subject, and then determining an IL-8 level in the blood or serum of the subject again;

wherein said condition is determined to be unresponsive to the agent if the IL-8 level does not decrease after the administration relative to before the administration; and wherein the condition is determined to be responsive to the agent if IL-8 level does decrease after the administration relative to before the administration.

2. The method of claim 1 wherein the subject is human and the agent is represented by a structural formula selected from the group consisting of:

A1

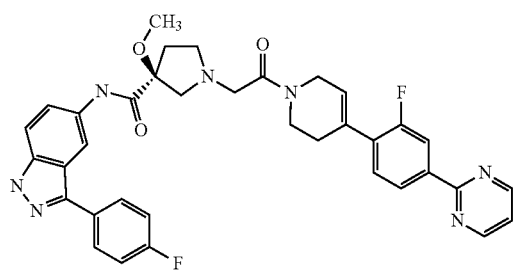

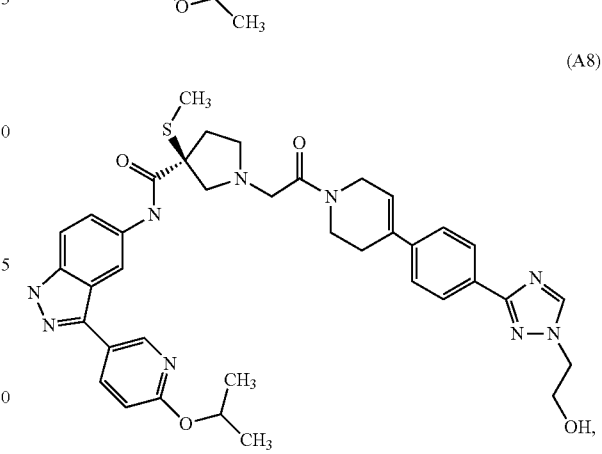

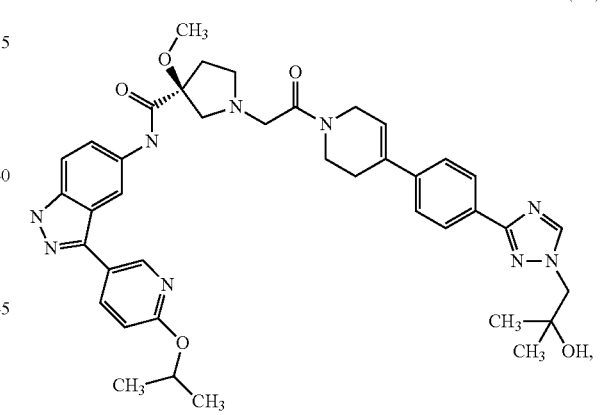

(A4)

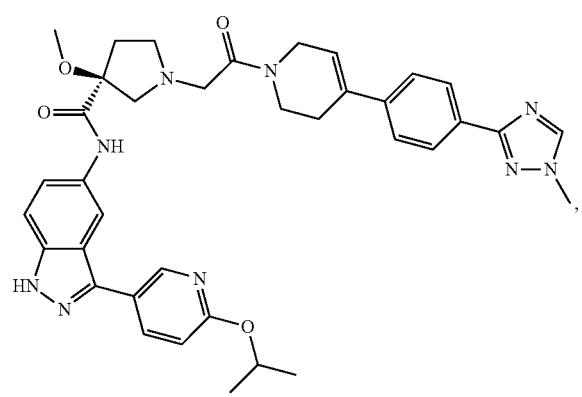

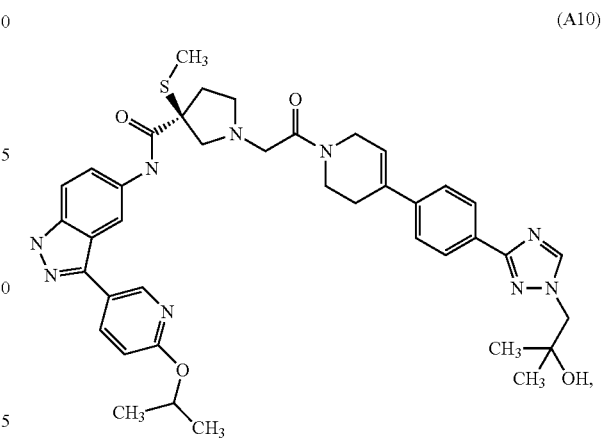

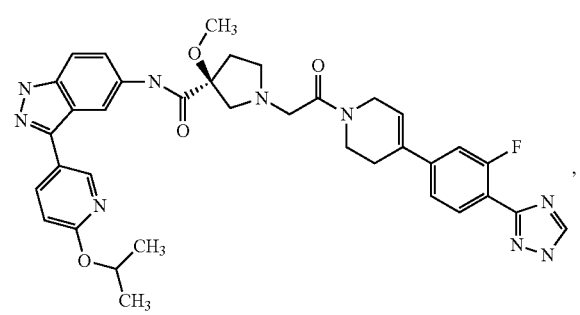

-continued
(A12)
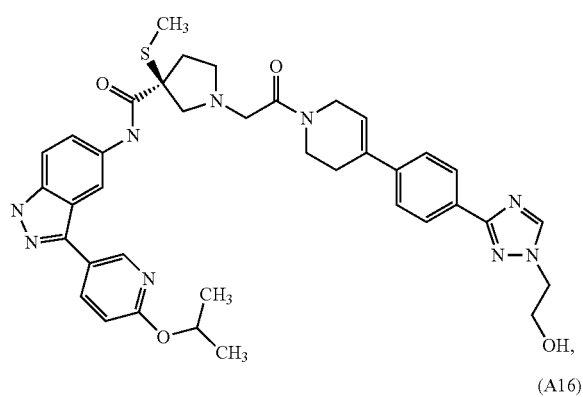
(A16)
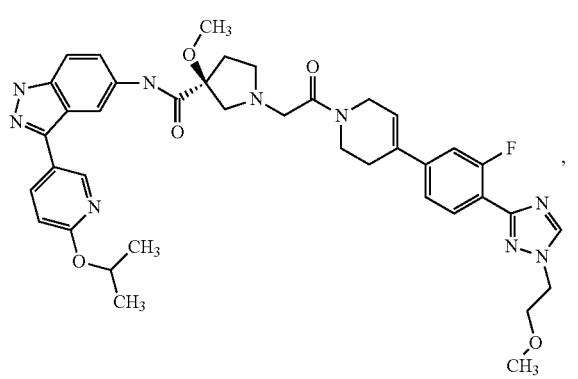
(A20)
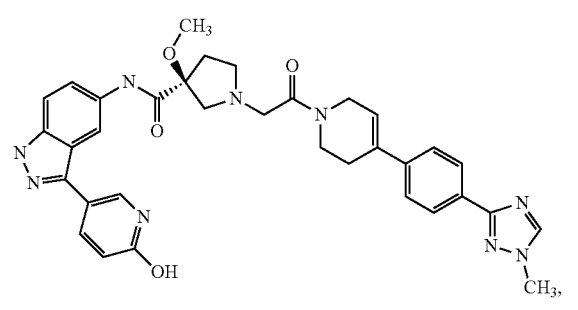
(A21)
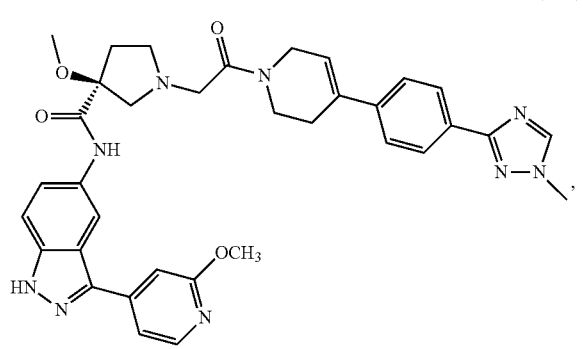
-continued
(A22)
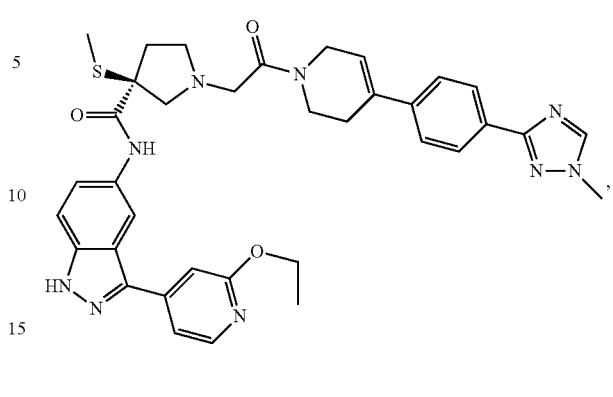
(A23)
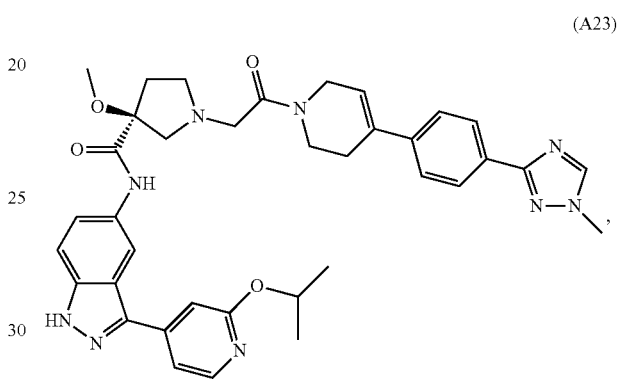
(A24)
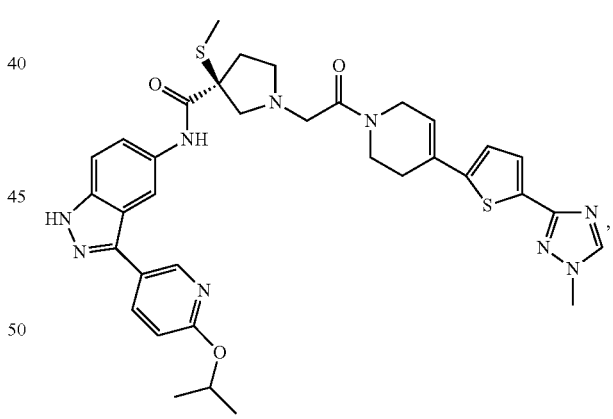
(A27)
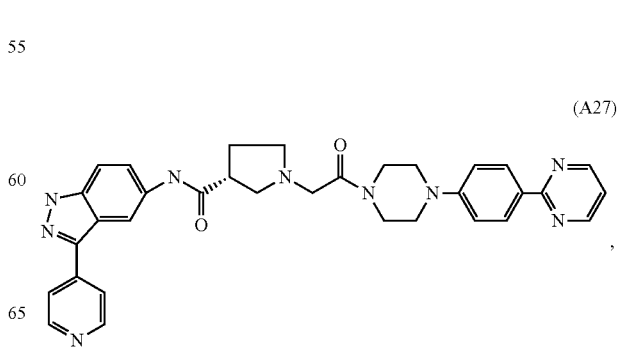

(A30)
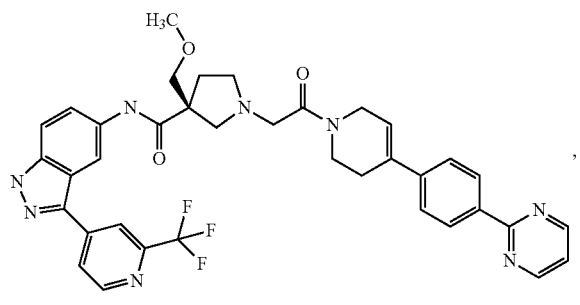
(A36)
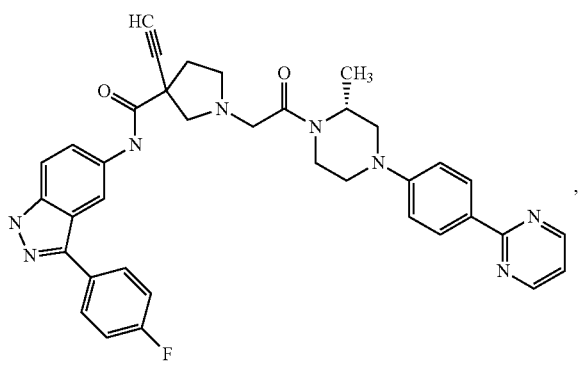
(A37)
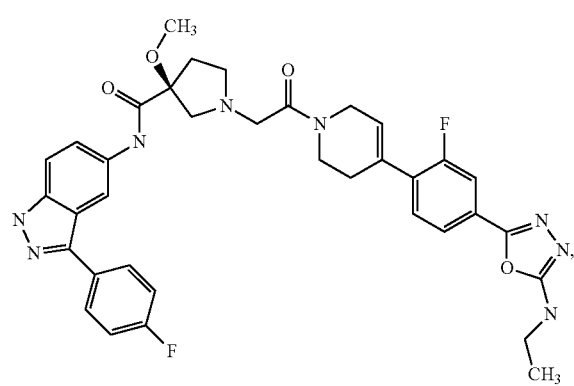
(A38)
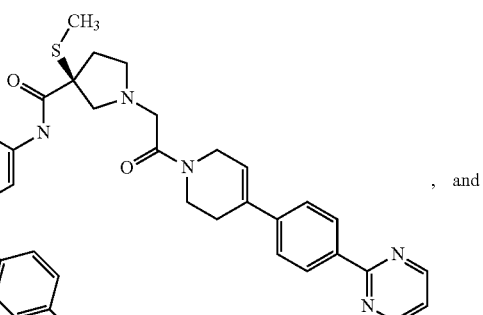
, and
(A39)
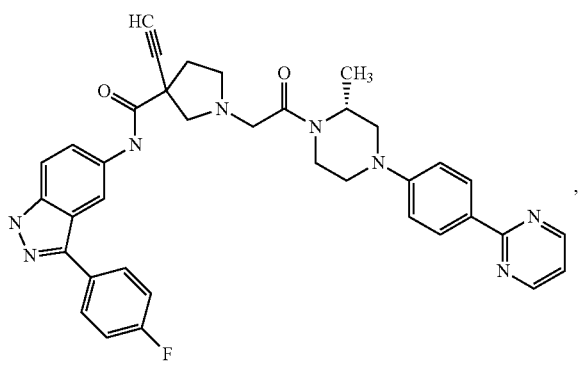
3. A method for determining if a subject with a malignant tumor or blood cancer has a malignant tumor or blood cancer that is responsive to an agent selected from the group consisting of:
(A1)
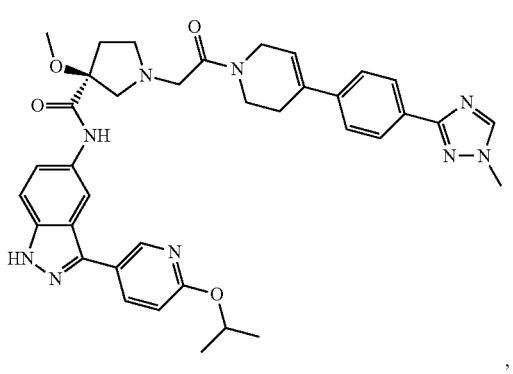
(A2)
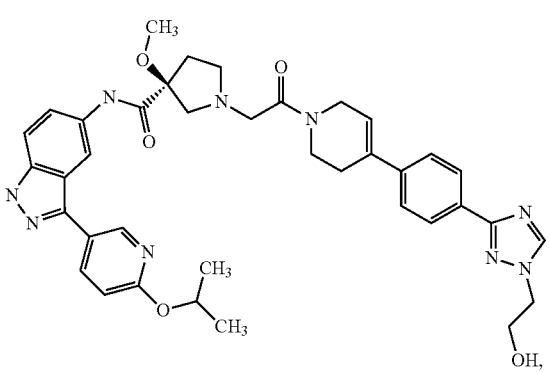

-continued
(A3)
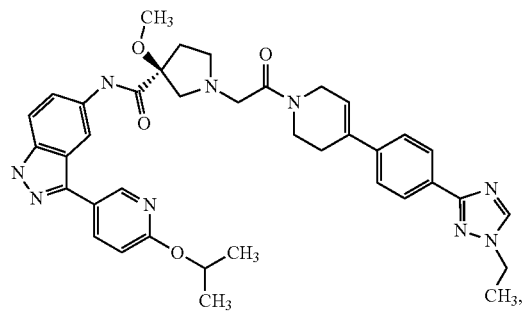
(A4)
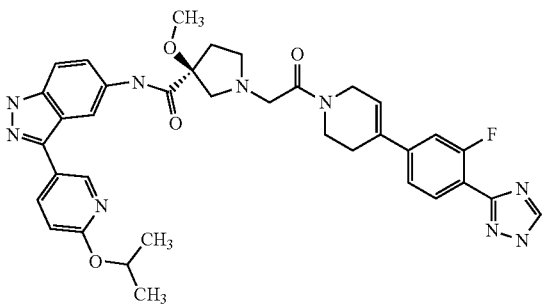
(A5)
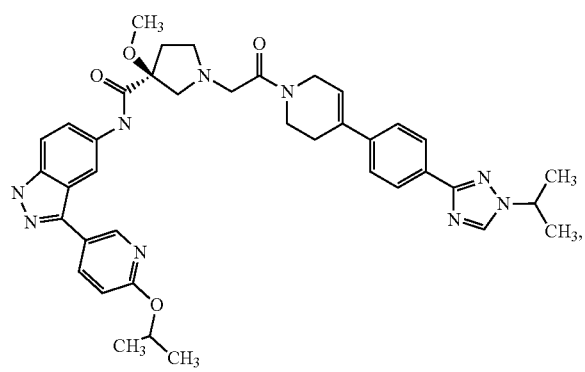
(A6)
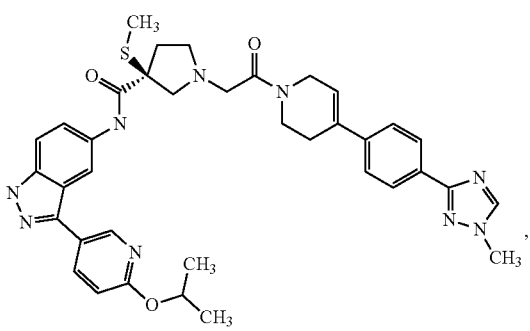
(A7)
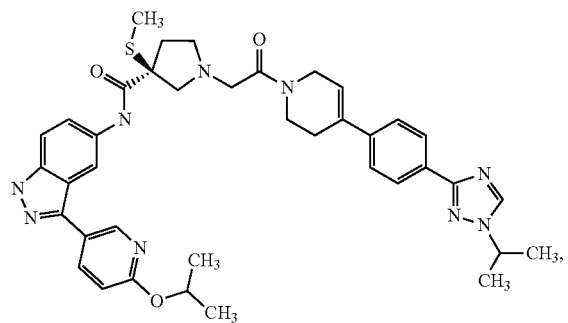
(A8)
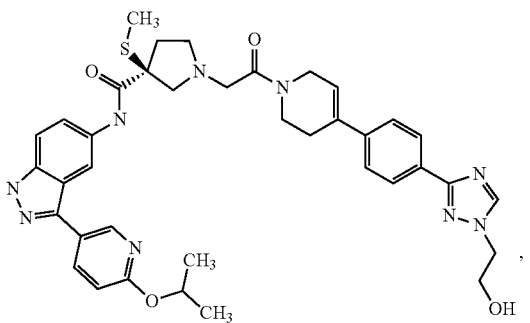
(A9)
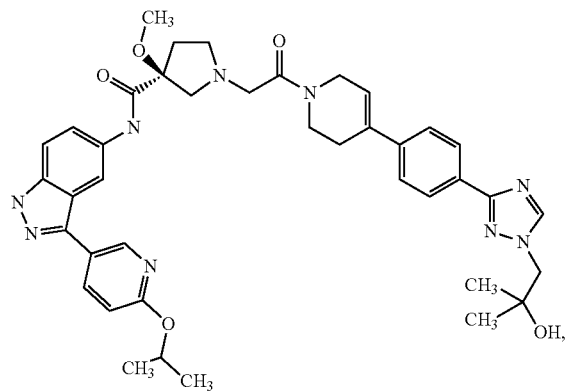
(A10)
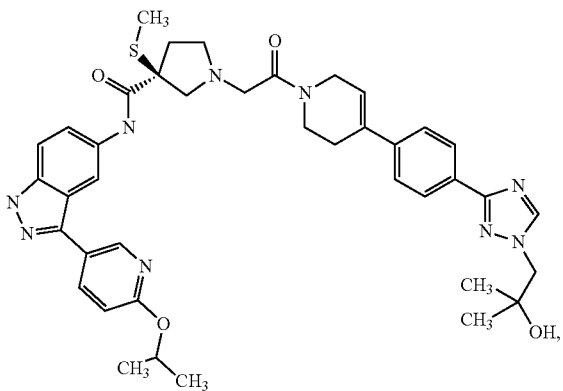

-continued
(A11)
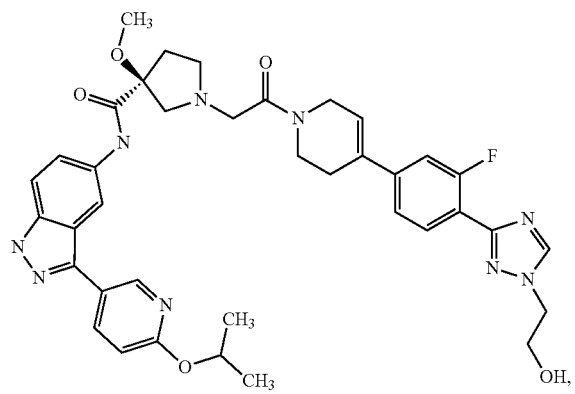
(A12)
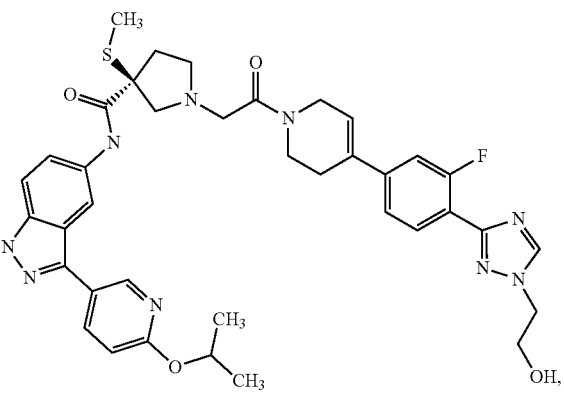
(A13)
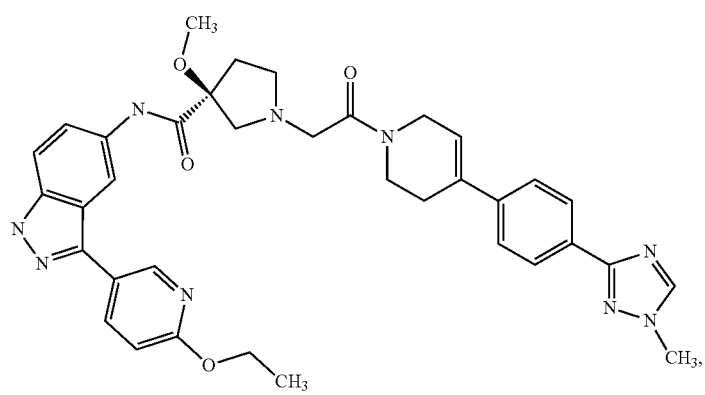
(A14)
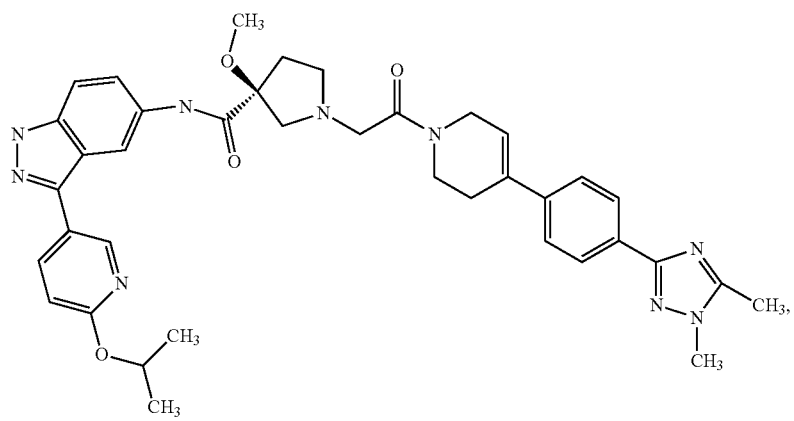
(A15)
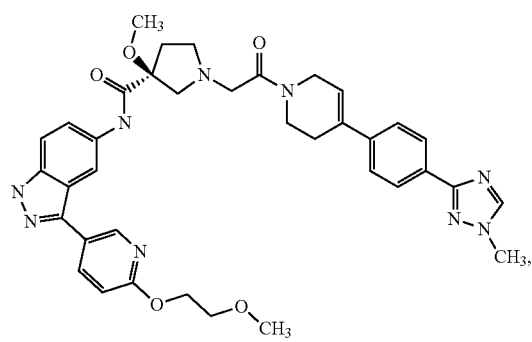
(A16)
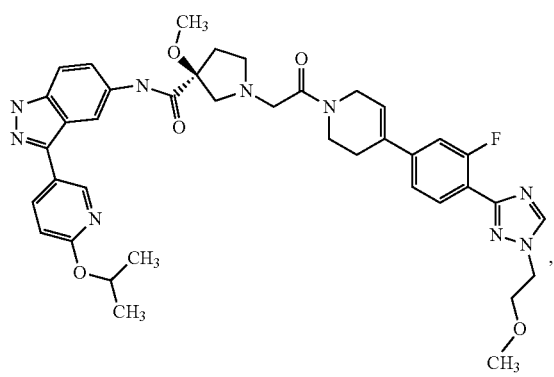

-continued
(A18)
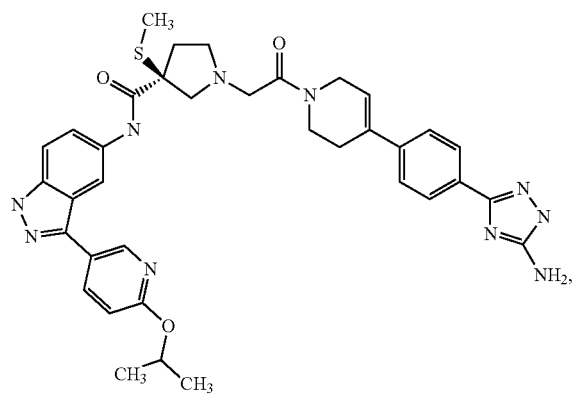
(A20)
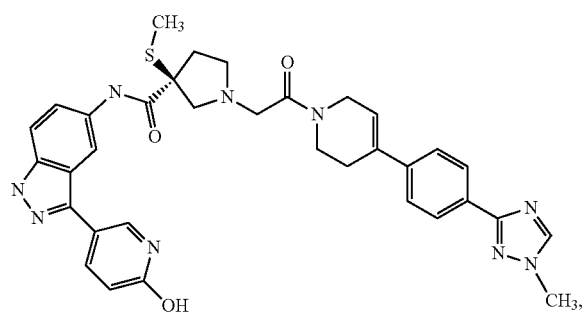
(A21)
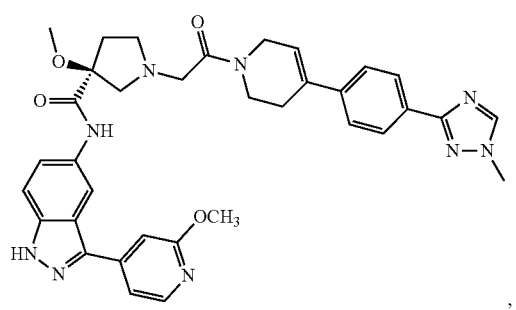
(A22)
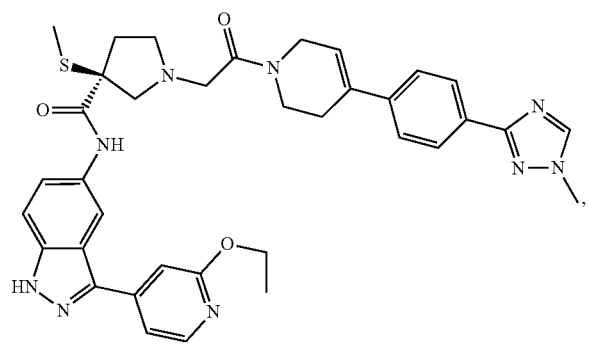
(A23)
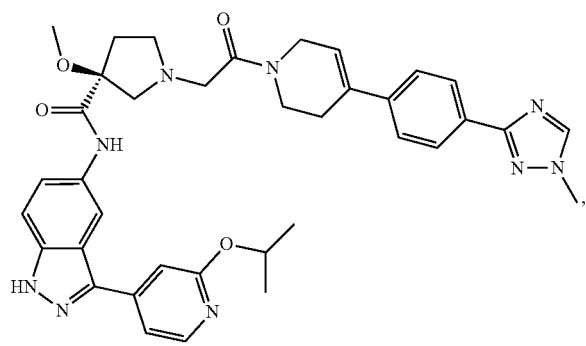
(A24)
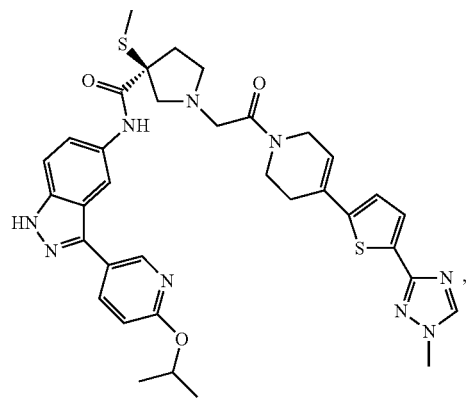
(A25)
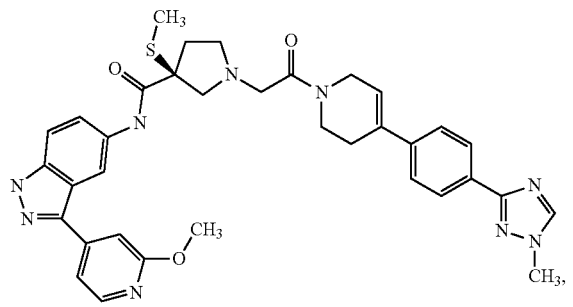

-continued
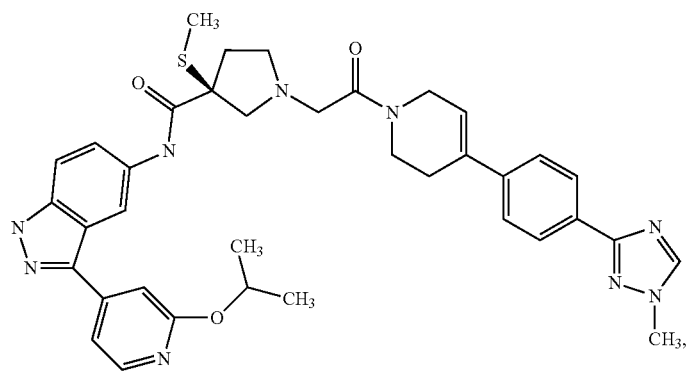
(A26)
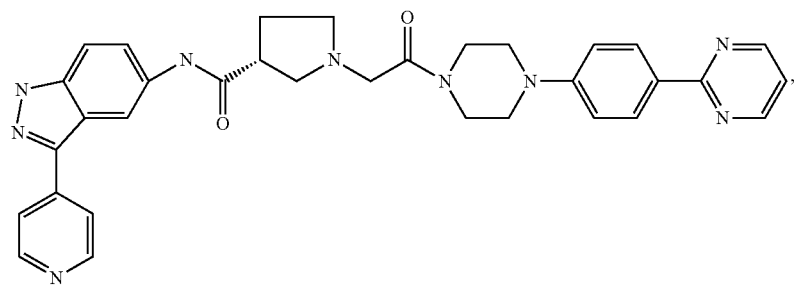
(A27)
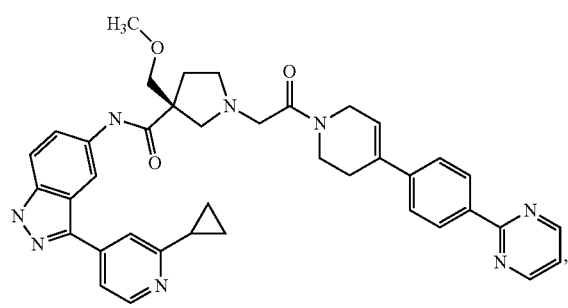
(A28)
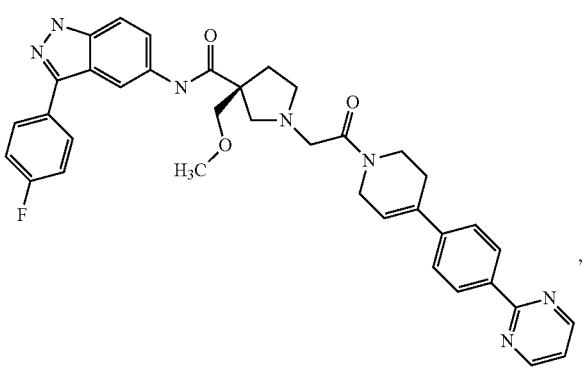
(A29)
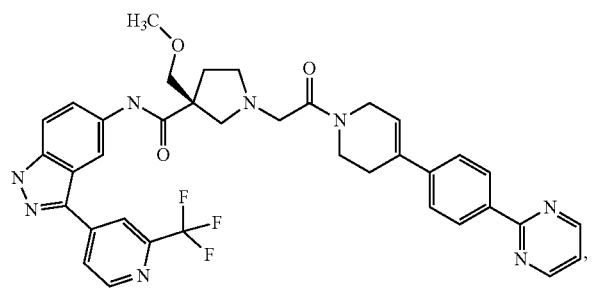
(A30)
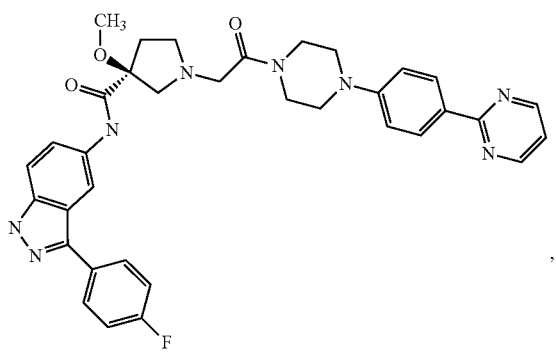
(A31)

-continued
(A32)
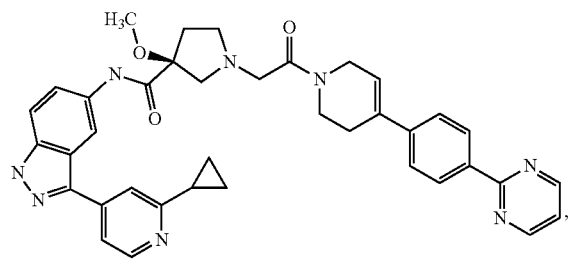
(A33)
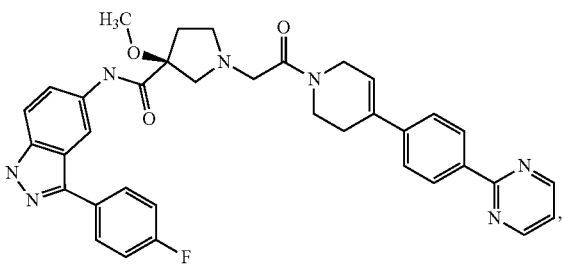
(A34)
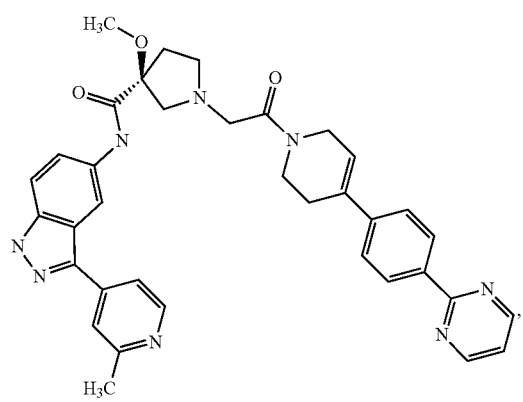
(A35)
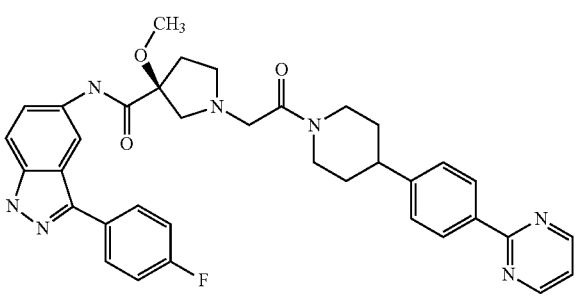
(A36)
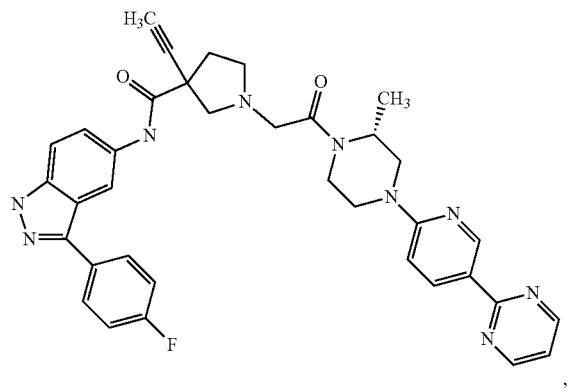
(A37)
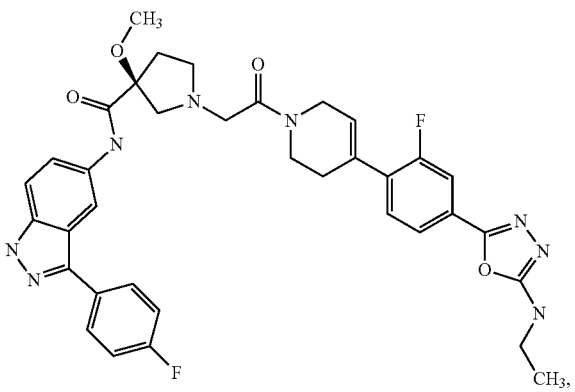
(A38)
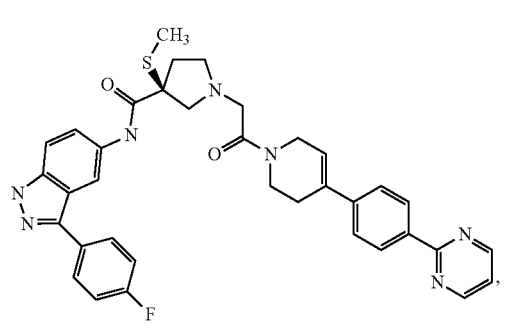
and (A39)

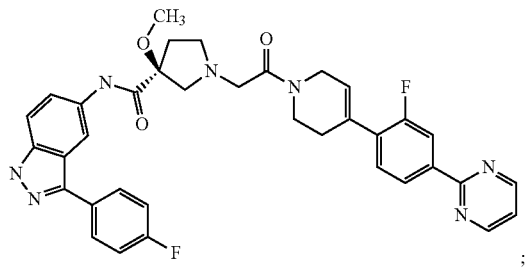

;

wherein the tumor or blood cancer is a member selected from the group consisting of: lung cancer, lung adenocarcinoma, non small cell lung cancer, pancreatic cancer, pancreatic carcinoma, exocrine pancreatic carcinoma, colon cancer, colorectal carcinoma, colon adenocarcinoma, myeloid leukemia, acute myelogenous leukemia, chronic myelogenous leukemia, chronic myelomonocytic leukemia, thyroid cancer, bladder carcinoma, epidermal carcinoma, melanoma, breast cancer, prostate cancer, head and neck cancer, squamous cell cancer of the head and neck, ovarian cancer, brain cancer, glioma, glioma blastoma multiforme, cancer of mesenchymal origin, fibrosarcoma, rhabdomyosarcoma, sarcoma, teratocarcinoma, neuroblastoma, kidney carcinoma, hepatoma, non-Hodgkin's lymphoma, multiple myeloma, and anaplastic thyroid carcinoma;

comprising determining an IL-8 level in the blood or serum of the subject, administering the agent to the subject, and then determining an IL-8 level in the blood or serum of the subject again;

wherein said condition is determined to be unresponsive to the agent if the IL-8 level does not decrease after the administration relative to before the administration; and wherein the condition is determined to be responsive to the agent if the IL-8 level does decrease after the administration relative to before the administration.

4. The method of claim 3 wherein the subject is human and the malignant tumor is melanoma.

5. The method of claim 3 wherein the agent is represented by the structural formula:

A1

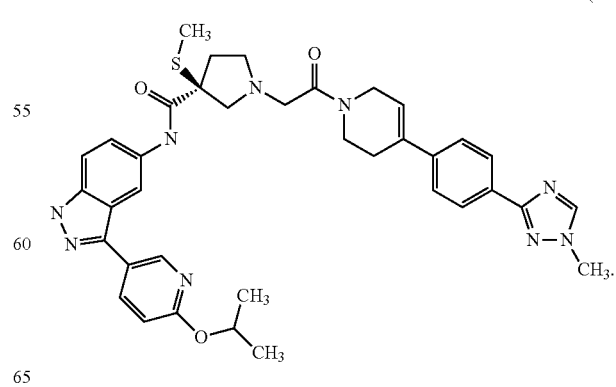

6. The method of claim 3 wherein the agent is represented by the structural formula:

(A4)

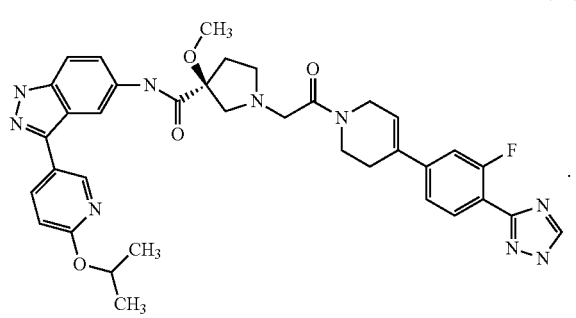

.

7. The method of claim 3 wherein the agent is represented by the structural formula:

(A6)

8. The method of claim 3 wherein the agent is represented by the structural formula:

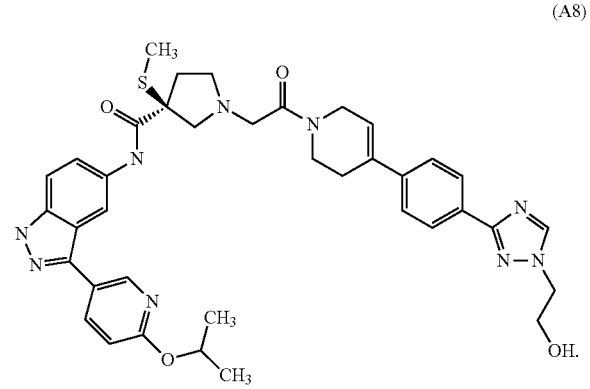 [SMILES: CS[C@@]1(C(=O)Nc2ccc3[nH]nc(-c4ccc(OC(C)C)nc4)c3c2)CCN(CC(=O)N2CC=C(c3ccc(-c4ncn(CCO)n4)cc3)CC2)C1]

(A8)

9. The method of claim 3 wherein the agent is represented by the structural formula:

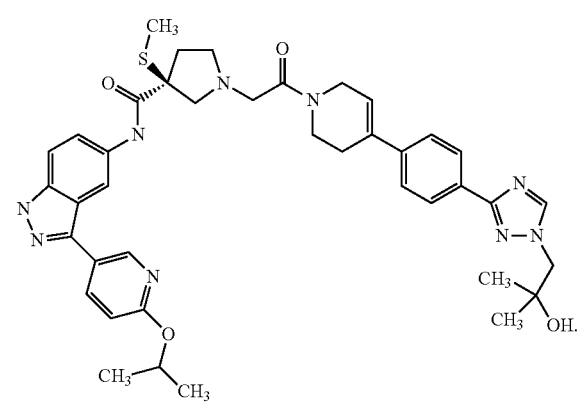

(A9)

10. The method of claim 3 wherein the agent is represented by the structural formula:

(A10)

11. The method of claim 3 wherein the agent is represented by the structural formula:

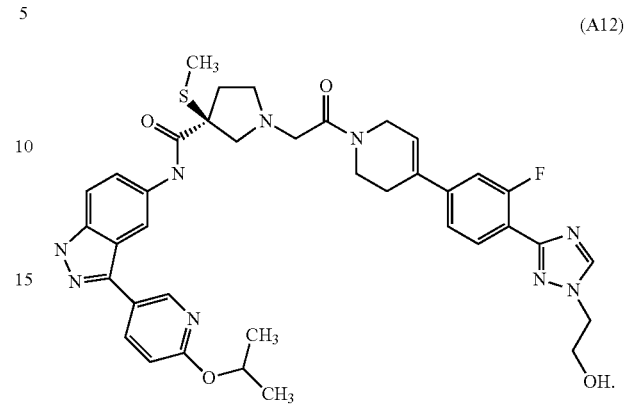

(A12)

12. The method of claim 3 wherein the agent is represented by the structural formula:

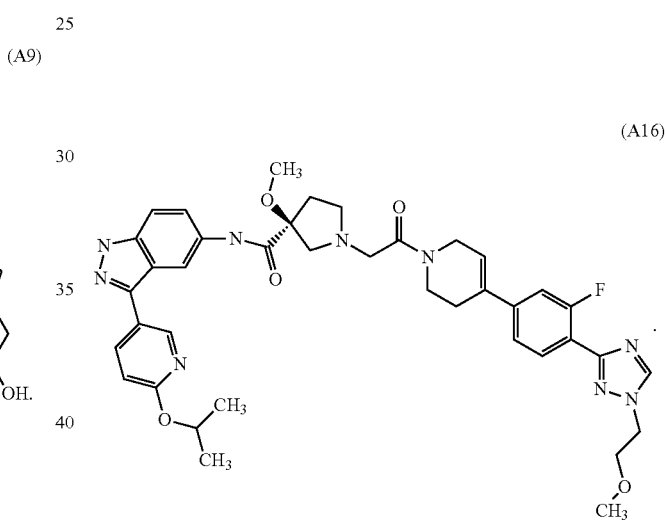

(A16)

13. The method of claim 3 wherein the agent is represented by the structural formula:

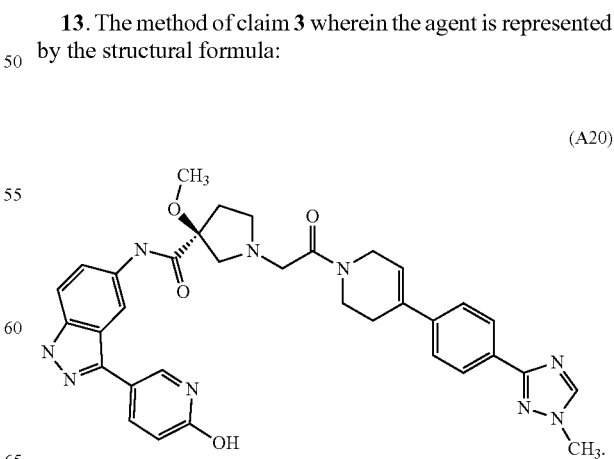

(A20)

14. The method of claim 3 wherein the agent is represented by the structural formula:

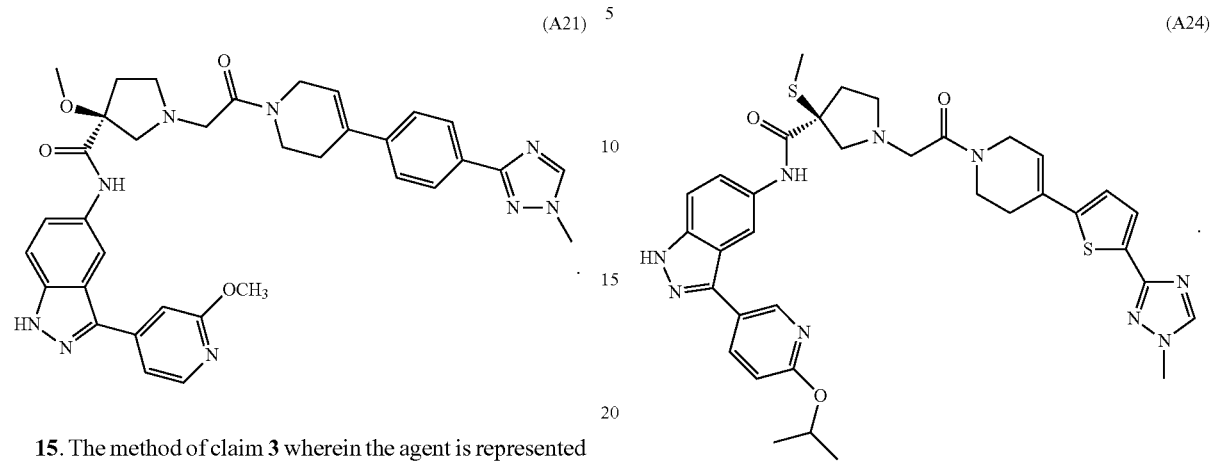

(A21)

15. The method of claim 3 wherein the agent is represented by the structural formula:

(A22)

16. The method of claim 3 wherein the agent is represented by the structural formula:

(A23)

17. The method of claim 3 wherein the agent is represented by the structural formula:

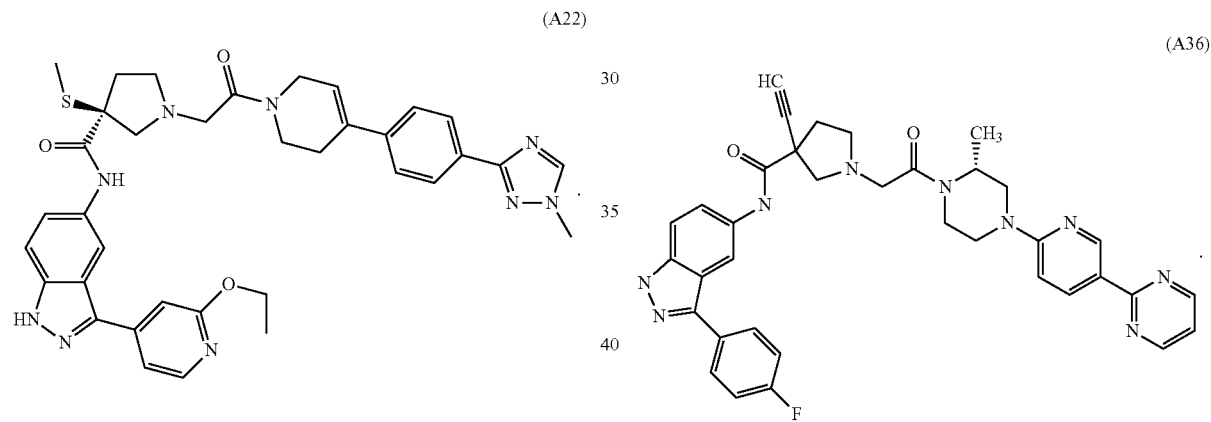

(A24)

18. The method of claim 3 wherein the agent is represented by the structural formula:

(A36)

19. The method of claim 3 wherein the agent is represented by the structural formula:

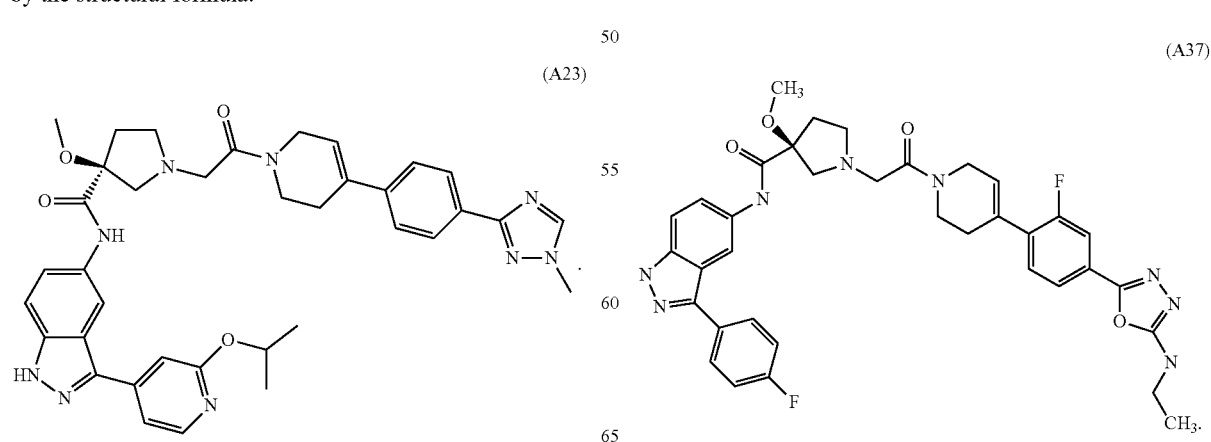

(A37)

20. The method of claim 3 wherein the agent is represented by the structural formula:
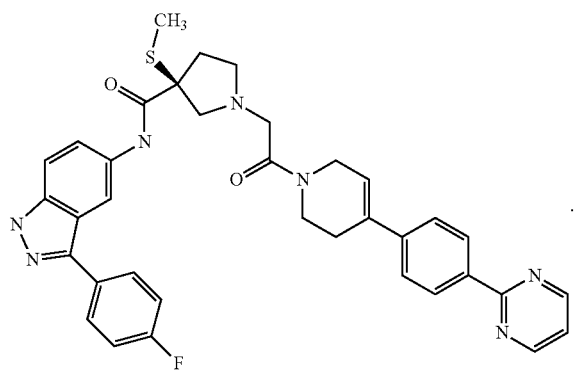
(A38)
21. The method of claim 3 wherein the agent is represented by the structural formula:
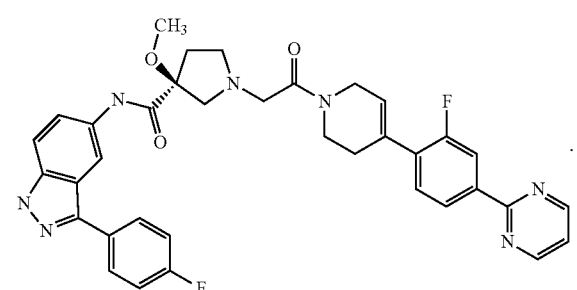
(A39)
* * * * *

SEQUENCE LISTING

<160> NUMBER OF SEQ ID NOS: 6

<210> SEQ ID NO 1
<211> LENGTH: 300
<212> TYPE: DNA
<213> ORGANISM: Homo sapiens
<220> FEATURE:
<221> NAME/KEY: CDS
<222> LOCATION: (1)..(300)

<400> SEQUENCE: 1

| | | | | | | | | | | | | | | | | |
|---|---|---|---|---|---|---|---|---|---|---|---|---|---|---|---|---|
| atg | act | tcc | aag | ctg | gcc | gtg | gct | ctc | ttg | gca | gcc | ttc | ctg | att | tct | 48 |
| Met | Thr | Ser | Lys | Leu | Ala | Val | Ala | Leu | Leu | Ala | Ala | Phe | Leu | Ile | Ser | |
| 1 | | | | 5 | | | | | 10 | | | | | 15 | | |

| gca | gct | ctg | tgt | gaa | ggt | gca | gtt | ttg | cca | agg | agt | gct | aaa | gaa | ctt | 96 |
|---|---|---|---|---|---|---|---|---|---|---|---|---|---|---|---|---|
| Ala | Ala | Leu | Cys | Glu | Gly | Ala | Val | Leu | Pro | Arg | Ser | Ala | Lys | Glu | Leu | |
| | | | 20 | | | | | 25 | | | | | 30 | | | |

| aga | tgt | cag | tgc | ata | aag | aca | tac | tcc | aaa | cct | ttc | cac | ccc | aaa | ttt | 144 |
|---|---|---|---|---|---|---|---|---|---|---|---|---|---|---|---|---|
| Arg | Cys | Gln | Cys | Ile | Lys | Thr | Tyr | Ser | Lys | Pro | Phe | His | Pro | Lys | Phe | |
| | | 35 | | | | | 40 | | | | | 45 | | | | |

| atc | aaa | gaa | ctg | aga | gtg | att | gag | agt | gga | cca | cac | tgc | gcc | aac | aca | 192 |
|---|---|---|---|---|---|---|---|---|---|---|---|---|---|---|---|---|
| Ile | Lys | Glu | Leu | Arg | Val | Ile | Glu | Ser | Gly | Pro | His | Cys | Ala | Asn | Thr | |
| 50 | | | | | 55 | | | | | 60 | | | | | | |

| gaa | att | att | gta | aag | ctt | tct | gat | gga | aga | gag | ctc | tgt | ctg | gac | ccc | 240 |
|---|---|---|---|---|---|---|---|---|---|---|---|---|---|---|---|---|
| Glu | Ile | Ile | Val | Lys | Leu | Ser | Asp | Gly | Arg | Glu | Leu | Cys | Leu | Asp | Pro | |
| 65 | | | | | 70 | | | | | 75 | | | | | 80 | |

| aag | gaa | aac | tgg | gtg | cag | agg | gtt | gtg | gag | aag | ttt | ttg | aag | agg | gct | 288 |
|---|---|---|---|---|---|---|---|---|---|---|---|---|---|---|---|---|
| Lys | Glu | Asn | Trp | Val | Gln | Arg | Val | Val | Glu | Lys | Phe | Leu | Lys | Arg | Ala | |
| | | | 85 | | | | | 90 | | | | | 95 | | | |

| gag | aat | tca | taa | 300 |
|---|---|---|---|---|
| Glu | Asn | Ser | | |

<210> SEQ ID NO 2
<211> LENGTH: 99
<212> TYPE: PRT
<213> ORGANISM: Homo sapiens

<400> SEQUENCE: 2

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser

<210> SEQ ID NO 3
<211> LENGTH: 1140
<212> TYPE: DNA
<213> ORGANISM: Homo sapiens
<220> FEATURE:
<221> NAME/KEY: CDS
<222> LOCATION: (1)..(1140)

<400> SEQUENCE: 3

```
atg gcg gcg gcg gcg gct cag ggg ggc ggg ggc ggg gag ccc cgt aga        48
Met Ala Ala Ala Ala Ala Gln Gly Gly Gly Gly Gly Glu Pro Arg Arg
1               5                   10                  15 acc gag ggg gtc ggc ccg ggg gtc ccg ggg gag gtg gag atg gtg aag        96
Thr Glu Gly Val Gly Pro Gly Val Pro Gly Glu Val Glu Met Val Lys
                20                  25                  30 ggg cag ccg ttc gac gtg ggc ccg cgc tac acg cag ttg cag tac atc       144
Gly Gln Pro Phe Asp Val Gly Pro Arg Tyr Thr Gln Leu Gln Tyr Ile
            35                  40                  45 ggc gag ggc gcg tac ggc atg gtc agc tcg gcc tat gac cac gtg cgc       192
Gly Glu Gly Ala Tyr Gly Met Val Ser Ser Ala Tyr Asp His Val Arg
        50                  55                  60 aag act cgc gtg gcc atc aag aag atc agc ccc ttc gaa cat cag acc       240
Lys Thr Arg Val Ala Ile Lys Lys Ile Ser Pro Phe Glu His Gln Thr
65                  70                  75                  80 tac tgc cag cgc acg ctc cgg gag atc cag atc ctg ctg cgc ttc cgc       288
Tyr Cys Gln Arg Thr Leu Arg Glu Ile Gln Ile Leu Leu Arg Phe Arg
                85                  90                  95 cat gag aat gtc atc ggc atc cga gac att ctg cgg gcg tcc acc ctg       336
His Glu Asn Val Ile Gly Ile Arg Asp Ile Leu Arg Ala Ser Thr Leu
            100                 105                 110 gaa gcc atg aga gat gtc tac att gtg cag gac ctg atg gag act gac       384
Glu Ala Met Arg Asp Val Tyr Ile Val Gln Asp Leu Met Glu Thr Asp
        115                 120                 125 ctg tac aag ttg ctg aaa agc cag cag ctg agc aat gac cat atc tgc       432
Leu Tyr Lys Leu Leu Lys Ser Gln Gln Leu Ser Asn Asp His Ile Cys
    130                 135                 140 tac ttc ctc tac cag atc ctg cgg ggc ctc aag tac atc cac tcc gcc       480
Tyr Phe Leu Tyr Gln Ile Leu Arg Gly Leu Lys Tyr Ile His Ser Ala
145                 150                 155                 160 aac gtg ctc cac cga gat cta aag ccc tcc aac ctg ctc atc aac acc       528
Asn Val Leu His Arg Asp Leu Lys Pro Ser Asn Leu Leu Ile Asn Thr
                165                 170                 175 acc tgc gac ctt aag att tgt gat ttc ggc ctg gcc cgg att gcc gat       576
Thr Cys Asp Leu Lys Ile Cys Asp Phe Gly Leu Ala Arg Ile Ala Asp
            180                 185                 190 cct gag cat gac cac acc ggc ttc ctg acg gag tat gtg gct acg cgc       624
Pro Glu His Asp His Thr Gly Phe Leu Thr Glu Tyr Val Ala Thr Arg
        195                 200                 205 tgg tac cgg gcc cca gag atc atg ctg aac tcc aag ggc tat acc aag       672
Trp Tyr Arg Ala Pro Glu Ile Met Leu Asn Ser Lys Gly Tyr Thr Lys
    210                 215                 220 tcc atc gac atc tgg tct gtg ggc tgc att ctg gct gag atg ctc tct       720
Ser Ile Asp Ile Trp Ser Val Gly Cys Ile Leu Ala Glu Met Leu Ser
225                 230                 235                 240 aac cgg ccc atc ttc cct ggc aag cac tac ctg gat cag ctc aac cac       768
Asn Arg Pro Ile Phe Pro Gly Lys His Tyr Leu Asp Gln Leu Asn His
                245                 250                 255 att ctg ggc atc ctg ggc tcc cca tcc cag gag gac ctg aat tgt atc       816
Ile Leu Gly Ile Leu Gly Ser Pro Ser Gln Glu Asp Leu Asn Cys Ile
            260                 265                 270 atc aac atg aag gcc cga aac tac cta cag tct ctg ccc tcc aag acc       864
Ile Asn Met Lys Ala Arg Asn Tyr Leu Gln Ser Leu Pro Ser Lys Thr
        275                 280                 285 aag gtg gct tgg gcc aag ctt ttc ccc aag tca gac tcc aaa gcc ctt       912
Lys Val Ala Trp Ala Lys Leu Phe Pro Lys Ser Asp Ser Lys Ala Leu
    290                 295                 300 gac ctg ctg gac cgg atg tta acc ttt aac ccc aat aaa cgg atc aca       960
Asp Leu Leu Asp Arg Met Leu Thr Phe Asn Pro Asn Lys Arg Ile Thr
305                 310                 315                 320
```

```
gtg gag gaa gcg ctg gct cac ccc tac ctg gag cag tac tat gac ccg      1008
Val Glu Glu Ala Leu Ala His Pro Tyr Leu Glu Gln Tyr Tyr Asp Pro
            325                 330                 335 acg gat gag cca gtg gcc gag gag ccc ttc acc ttc gcc atg gag ctg      1056
Thr Asp Glu Pro Val Ala Glu Glu Pro Phe Thr Phe Ala Met Glu Leu
        340                 345                 350 gat gac cta cct aag gag cgg ctg aag gag ctc atc ttc cag gag aca      1104
Asp Asp Leu Pro Lys Glu Arg Leu Lys Glu Leu Ile Phe Gln Glu Thr
        355                 360                 365 gca cgc ttc cag ccc gga gtg ctg gag gcc ccc tag                      1140
Ala Arg Phe Gln Pro Gly Val Leu Glu Ala Pro
        370                 375

<210> SEQ ID NO 4
<211> LENGTH: 379
<212> TYPE: PRT
<213> ORGANISM: Homo sapiens

<400> SEQUENCE: 4

Met Ala Ala Ala Ala Gln Gly Gly Gly Gly Glu Pro Arg Arg
1               5                   10                  15

Thr Glu Gly Val Gly Pro Gly Val Pro Gly Glu Val Glu Met Val Lys
            20                  25                  30

Gly Gln Pro Phe Asp Val Gly Pro Arg Tyr Thr Gln Leu Gln Tyr Ile
        35                  40                  45

Gly Glu Gly Ala Tyr Gly Met Val Ser Ser Ala Tyr Asp His Val Arg
    50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
    130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
    210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285
```

```
Lys Val Ala Trp Ala Lys Leu Phe Pro Lys Ser Asp Ser Lys Ala Leu
290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Pro Phe Thr Phe Ala Met Glu Leu
                340                 345                 350

Asp Asp Leu Pro Lys Glu Arg Leu Lys Glu Leu Ile Phe Gln Glu Thr
                355                 360                 365

Ala Arg Phe Gln Pro Gly Val Leu Glu Ala Pro
370                 375
```

<210> SEQ ID NO 5
<211> LENGTH: 1083
<212> TYPE: DNA
<213> ORGANISM: Homo sapiens
<220> FEATURE:
<221> NAME/KEY: CDS
<222> LOCATION: (1)..(1083)

<400> SEQUENCE: 5

```
atg gcg gcg gcg gcg gcg ggc gcg ggc ccg gag atg gtc cgc ggg        48
Met Ala Ala Ala Ala Ala Gly Ala Gly Pro Glu Met Val Arg Gly
1               5                   10                  15 cag gtg ttc gac gtg ggg ccg cgc tac acc aac ctc tcg tac atc ggc   96
Gln Val Phe Asp Val Gly Pro Arg Tyr Thr Asn Leu Ser Tyr Ile Gly
            20                  25                  30 gag ggc gcc tac ggc atg gtg tgc tct gct tat gat aat gtc aac aaa  144
Glu Gly Ala Tyr Gly Met Val Cys Ser Ala Tyr Asp Asn Val Asn Lys
        35                  40                  45 gtt cga gta gct atc aag aaa atc agc ccc ttt gag cac cag acc tac  192
Val Arg Val Ala Ile Lys Lys Ile Ser Pro Phe Glu His Gln Thr Tyr
    50                  55                  60 tgc cag aga acc ctg agg gag ata aaa atc tta ctg cgc ttc aga cat  240
Cys Gln Arg Thr Leu Arg Glu Ile Lys Ile Leu Leu Arg Phe Arg His
65                  70                  75                  80 gag aac atc att gga atc aat gac att att cga gca cca acc atc gag  288
Glu Asn Ile Ile Gly Ile Asn Asp Ile Ile Arg Ala Pro Thr Ile Glu
                85                  90                  95 caa atg aaa gat gta tat ata gta cag gac ctc atg gaa aca gat ctt  336
Gln Met Lys Asp Val Tyr Ile Val Gln Asp Leu Met Glu Thr Asp Leu
            100                 105                 110 tac aag ctc ttg aag aca caa cac ctc agc aat gac cat atc tgc tat  384
Tyr Lys Leu Leu Lys Thr Gln His Leu Ser Asn Asp His Ile Cys Tyr
        115                 120                 125 ttt ctc tac cag atc ctc aga ggg tta aaa tat atc cat tca gct aac  432
Phe Leu Tyr Gln Ile Leu Arg Gly Leu Lys Tyr Ile His Ser Ala Asn
    130                 135                 140 gtt ctg cac cgt gac ctc aag cct tcc aac ctg ctg ctc aac acc acc  480
Val Leu His Arg Asp Leu Lys Pro Ser Asn Leu Leu Leu Asn Thr Thr
145                 150                 155                 160 tgt gat ctc aag atc tgt gac ttt ggc ctg gcc cgt gtt gca gat cca  528
Cys Asp Leu Lys Ile Cys Asp Phe Gly Leu Ala Arg Val Ala Asp Pro
                165                 170                 175 gac cat gat cac aca ggg ttc ctg aca gaa tat gtg gcc aca cgt tgg  576
Asp His Asp His Thr Gly Phe Leu Thr Glu Tyr Val Ala Thr Arg Trp
            180                 185                 190 tac agg gct cca gaa att atg ttg aat tcc aag ggc tac acc aag tcc  624
Tyr Arg Ala Pro Glu Ile Met Leu Asn Ser Lys Gly Tyr Thr Lys Ser
```

```
att gat att tgg tct gta ggc tgc att ctg gca gaa atg ctt tct aac        672
Ile Asp Ile Trp Ser Val Gly Cys Ile Leu Ala Glu Met Leu Ser Asn
210                 215                 220 agg ccc atc ttt cca ggg aag cat tat ctt gac cag ctg aac cac att        720
Arg Pro Ile Phe Pro Gly Lys His Tyr Leu Asp Gln Leu Asn His Ile
225                 230                 235                 240 ttg ggt att ctt gga tcc cca tca caa gaa gac ctg aat tgt ata ata        768
Leu Gly Ile Leu Gly Ser Pro Ser Gln Glu Asp Leu Asn Cys Ile Ile
                245                 250                 255 aat tta aaa gct agg aac tat ttg ctt tct ctt cca cac aaa aat aag        816
Asn Leu Lys Ala Arg Asn Tyr Leu Leu Ser Leu Pro His Lys Asn Lys
        260                 265                 270 gtg cca tgg aac agg ctg ttc cca aat gct gac tcc aaa gct ctg gac        864
Val Pro Trp Asn Arg Leu Phe Pro Asn Ala Asp Ser Lys Ala Leu Asp
            275                 280                 285 tta ttg gac aaa atg ttg aca ttc aac cca cac aag agg att gaa gta        912
Leu Leu Asp Lys Met Leu Thr Phe Asn Pro His Lys Arg Ile Glu Val
290                 295                 300 gaa cag gct ctg gcc cac cca tat ctg gag cag tat tac gac ccg agt        960
Glu Gln Ala Leu Ala His Pro Tyr Leu Glu Gln Tyr Tyr Asp Pro Ser
305                 310                 315                 320 gac gag ccc atc gcc gaa gca cca ttc aag ttc gac atg gaa ttg gat       1008
Asp Glu Pro Ile Ala Glu Ala Pro Phe Lys Phe Asp Met Glu Leu Asp
                325                 330                 335 gac ttg cct aag gaa aag ctc aaa gaa cta att ttt gaa gag act gct       1056
Asp Leu Pro Lys Glu Lys Leu Lys Glu Leu Ile Phe Glu Glu Thr Ala
                340                 345                 350 aga ttc cag cca gga tac aga tct taa                                   1083
Arg Phe Gln Pro Gly Tyr Arg Ser
            355                 360

<210> SEQ ID NO 6
<211> LENGTH: 360
<212> TYPE: PRT
<213> ORGANISM: Homo sapiens

<400> SEQUENCE: 6

Met Ala Ala Ala Ala Ala Gly Ala Gly Pro Glu Met Val Arg Gly
1               5                   10                  15

Gln Val Phe Asp Val Gly Pro Arg Tyr Thr Asn Leu Ser Tyr Ile Gly
                20                  25                  30

Glu Gly Ala Tyr Gly Met Val Cys Ser Ala Tyr Asp Asn Val Asn Lys
            35                  40                  45

Val Arg Val Ala Ile Lys Lys Ile Ser Pro Phe Glu His Gln Thr Tyr
        50                  55                  60

Cys Gln Arg Thr Leu Arg Glu Ile Lys Ile Leu Leu Arg Phe Arg His
65                  70                  75                  80

Glu Asn Ile Ile Gly Ile Asn Asp Ile Ile Arg Ala Pro Thr Ile Glu
                85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Leu Asn Thr Thr
145                 150                 155                 160
```

```
Cys Asp Leu Lys Ile Cys Asp Phe Gly Leu Ala Arg Val Ala Asp Pro
            165                 170                 175
Asp His Asp His Thr Gly Phe Leu Thr Glu Tyr Val Ala Thr Arg Trp
            180                 185                 190
Tyr Arg Ala Pro Glu Ile Met Leu Asn Ser Lys Gly Tyr Thr Lys Ser
            195                 200                 205
Ile Asp Ile Trp Ser Val Gly Cys Ile Leu Ala Glu Met Leu Ser Asn
            210                 215                 220
Arg Pro Ile Phe Pro Gly Lys His Tyr Leu Asp Gln Leu Asn His Ile
225                 230                 235                 240
Leu Gly Ile Leu Gly Ser Pro Ser Gln Glu Asp Leu Asn Cys Ile Ile
            245                 250                 255
Asn Leu Lys Ala Arg Asn Tyr Leu Leu Ser Leu Pro His Lys Asn Lys
            260                 265                 270
Val Pro Trp Asn Arg Leu Phe Pro Asn Ala Asp Ser Lys Ala Leu Asp
            275                 280                 285
Leu Leu Asp Lys Met Leu Thr Phe Asn Pro His Lys Arg Ile Glu Val
            290                 295                 300
Glu Gln Ala Leu Ala His Pro Tyr Leu Glu Gln Tyr Tyr Asp Pro Ser
305                 310                 315                 320
Asp Glu Pro Ile Ala Glu Ala Pro Phe Lys Phe Asp Met Glu Leu Asp
            325                 330                 335
Asp Leu Pro Lys Glu Lys Leu Lys Glu Leu Ile Phe Glu Glu Thr Ala
            340                 345                 350
Arg Phe Gln Pro Gly Tyr Arg Ser
            355                 360
```